United States Patent
Kalopissis et al.

[11] 3,953,508
[45] Apr. 27, 1976

[54] DIPHENYLAMINES FOR DYEING KERATINOUS FIBERS

[75] Inventors: Gregoire Kalopissis, Paris; Andrée Bugaut, Boulogne-sur-Seine; Françoise Estradier, Paris, all of France

[73] Assignee: L'Oreal, Paris, France

[22] Filed: Jan. 14, 1974

[21] Appl. No.: 432,982

Related U.S. Application Data

[60] Continuation-in-part of Ser. No. 301,715, Oct. 30, 1972, abandoned, which is a division of Ser. No. 61,833, Aug. 6, 1970, Pat. No. 3,792,090.

[30] Foreign Application Priority Data

Aug. 11, 1969 Luxemburg............................ 59265

[52] U.S. Cl................................ 260/562 A; 8/10.1;
260/553 R; 260/562 P; 260/571; 260/396 N
[51] Int. Cl.².................................... C07C 103/34
[58] Field of Search..................... 260/562 A, 562 P

[56] References Cited
UNITED STATES PATENTS
3,660,486  5/1972  Thiele............................ 260/562 A

*Primary Examiner*—C. Davis
*Attorney, Agent, or Firm*—Cushman, Darby & Cushman

[57] ABSTRACT

Diphenylamines having the formula

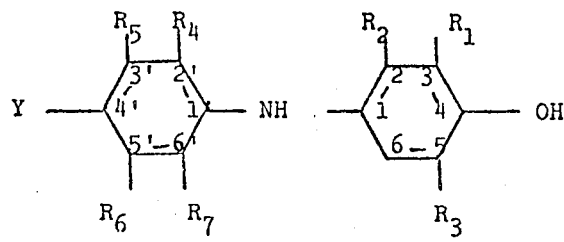

wherein: Y represents a member selected from the group consisting of a hydroxy and amino, $R_1$ and $R_3$, each independently, represent a member selected from the group consisting of hydrogen, halogen, lower alkyl, lower alkoxy, a ureido residue, and -NHCOR wherein R is lower alkyl, $R_2$ represents a member selected from the group consisting of hydrogen, halogen, lower alkyl, lower alkoxy, a ureido residue, -NHCOR wherein R is lower alkyl, and —$NHR_8$ wherein $R_8$ represents a member selected from the group consisting of hydrogen, lower alkyl, lower hydroxyalkyl and carbamyl lower alkyl, with the proviso that when $R_2$ is —$NHR_8$, $R_3$ is not hydrogen $R_4$, $R_5$, $R_6$, and $R_7$ each independently represent a member selected from the group consisting of hydrogen, halogen, lower alkyl and lower alkoxy, with the proviso that when Y is hydroxy, $R_2$ is not hydrogen, halogen, lower alkyl or alkoxy and that when Y is amino, at least two of $R_1$, $R_2$ and $R_3$ are other than a hydrogen and $R_2$ is not hydrogen when $R_4$, $R_5$, $R_6$ and $R_7$ are all hydrogen and the acid addition salts of said diphenylamines.

6 Claims, No Drawings

DIPHENYLAMINES FOR DYEING KERATINOUS FIBERS

This application is a continuation-in-part of our application Ser. No. 301,715 filed Oct. 30, 1972, and now abandoned, which in turn is a divisional of our application Ser. No. 61,833, filed Aug. 6, 1970, now U.S. Pat. No. 3,792,090.

This invention relates to novel diphenylamines and a process for preparing the same and to novel cosmetic composition containing diphenylamines for dyeing keratinic fibers such as human hair. More specifically, the present invention relates to a method and a use of a novel diphenylamine having the formula:

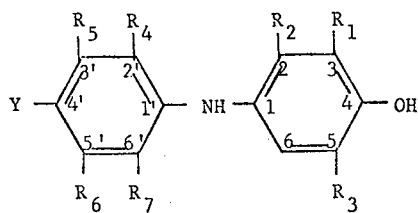

wherein: Y represents a member selected from the group consisting of hydroxy and amino, $R_1$ and $R_3$, each independently, represent a member selected from the group consisting of hydrogen, halogen, lower alkyl, lower alcoxy, ureido residue and —NHCOR group wherein R represents lower alkyl, $R_2$ represents a member selected from the group consisting of hydrogen, halogen, a lower alkyl, lower alkoxy, a ureido residue, —NHCOR wherein R represents lower alkyl and —NHR$_8$ wherein R$_8$ represents a member selected from the group consisting of hydrogen, a lower alkyl, lower hydroxy alkyl and carbamyl lower alkyl, with the proviso that when $R_2$ is —NHR$_8$, $R_3$ is not hydrogen, $R_4$, $R_5$, $R_6$, $R_7$ each represent a member selected from the group consisting of hydrogen, halogen, lower alkyl, lower alkoxy, with the proviso that when Y is hydroxy, $R_2$ is not hydrogen, halogen, lower alkyl, or alkoxy radical, and that when Y is amino, at least two of the radicals $R_1$, $R_2$ and $R_3$ are other than hydrogen and $R_2$ is not hydrogen when $R_4$, $R_5$, $R_6$, $R_7$ are all hydrogen, and the addition of salts of said diphenylamines with organic or inorganic acids.

In the above definition the terms lower alkyl and lower alkoxy radicals designate groups containing from 1 to 4 carbon atoms.

The diphenylamines of the present invention can be prepared by reducing an indoaniline or an indophenol having the formula:

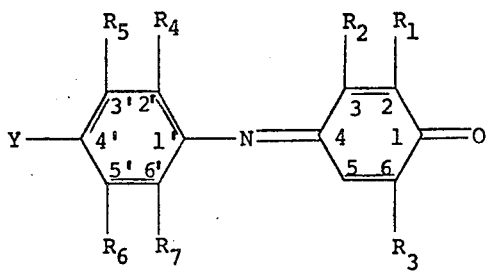

wherein $R_1$, $R_2$, $R_3$, $R_4$, $R_5$, $R_6$, $R_7$ and Y have the meanings given above in an alkaline medium having a pH ranging from about 9 to 12, and in the presence of effective amounts of a reducing agent selected from the group consisting of sodium hyposulfite or an alkaline sulfide such as sodium or ammonium sulfide. The amount of reducing agent can vary but generally it will be present in amounts such that the mole ratio of indoaniline or indophenol being reduced to reducing agent ranges between 1 : 1.5 to 1 : 3. The reducing reaction is generally carried out at ambient pressure and at a temperature ranging from about 25° to 50°C.

The reducing of the above indoaniline or indophenol can also be carried out by catalytic hydrogenation, under atmospheric pressure, in the presence of Pd on charcoal (10% Pd on charcoal).

The leucoderivatives of the present invention are colorless compounds which when applied in an aqueous medium to the fibers to be dyed, oxidize in the air or in the presence of added oxidizing agents, thereby yielding the corresponding indoanilines or indophenols, which are colored compounds and which are directly responsible for the coloring of the keratinic fibers. An important advantage of these leucoderivatives over their corresponding oxidation products are their increased solubility in an aqueous medium and hence their greater fiber penetrating characteristics. Because of these properties a better quality and a greater intensity of fiber coloring is attainable.

The applicants have also found that these diphenylamine leucoderivatives, as well as known diphenylamines of closely related structure, are advantageously employed in the preparation of keratinous fiber dyeing compositions and of capillary hair-setting lotions. Consequently, the present invention also has for its object the provision of (1) a dyeing composition for keratinous fibers, in particular for human hair characterized in that they contain in an aqueous or dilute alcohol solution at least one compound having the formula

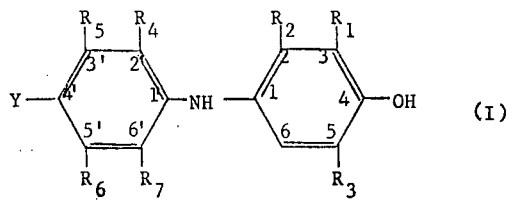  (I)

wherein: Y, $R_1$, $R_3$, $R_4$, $R_5$, $R_6$ and $R_7$ have the meanings indicated above and $R_2$ represents a member selected from the group consisting of hydrogen, halogen, lower alkyl, lower alkoxy, a ureido residue, —NHCOR wherein R is lower alkyl, and —NHR$_8$ wherein R$_8$ represents a member selected from the group consisting of hydrogen, lower alkyl, lower hydroxyalkyl and carbamylmethyl, with the proviso that when Y is amino, $R_2$ is not hydrogen when $R_1$, $R_2$, $R_3$, $R_4$, $R_7$ and $R_5$ or $R_6$ are all hydrogen.

The dyeing composition according to the invention can contain only the compounds of formula (I), or also other leucoderivatives or other dyes. The coloring can develop on the fibers under the sole action of the oxygen in the air, or again under the action of another oxidizing agent such as hydrogen peroxide, the latter being able to be incorporated in the compositions of this invention at the time of their application to the hair.

The pH of the dye composition according to the invention can vary between 4 and 11, and is generally between 7 and 11. To regulate this pH at the desired value, it is possible to use as alkalizing agents, ammonia, mono-, di- or triethanolamine, 2-amino-2-methylpropanol and as acidifying agents, phosphoric acid, acetic acid or lactic acid.

The dye compositions according to the invention contains from 0.01 to 1 and generally from 0.03 to 0.5% by weight of the diphenylamine leucoderivatives defined above.

The dye compositions according to the invention can be in aqueous solutions to which, if desired, there can be added low molecular weight alcohols such as ethanol or isopropanol, in amounts of 20 to 70% by weight, or again glycols such as propyleneglycol or butylglycol, in amounts of 1 to 6% by weight. These alcohols and glycols facilitate the use of the diphenylamines of formula (I).

The dye compositions according to the invention can also contain other known leucoderivatives of indoanilines, indamines or indophenols. They can also contain direct dyes such as nitro dyes of the benzene series, azo dyes, anthraquinone dyes, oxazines or azines.

Further the compositions according to the invention can contain various ingredients usually used in capillary cosmetics, such as, wetting agents, dispersing agents, penetrating agents, thickeners or perfumes. They can, on the other hand, be in the form of creams or gels, or packaged under pressure in aerosol bombs or containers, together with a conventional aerosol propellant such as dichlorodifluoromethane, trichloromonofluoromethane and their mixtures. Obviously other conventional aerosol propellants can be used.

Dyeing of keratinous fibers, in particular human hair, with the dye compositions according to the invention, can be performed in the usual way, by application of the composition to the fibers to be dyed, the composition being left in contact with the fibers for a time varying from 10 to 30 minutes. Following this application, the fibers can be rinsed and if desired washed. Thereafter, the thus treated fibers are dried. If desired, there can be added to the composition, before its application, either 20 to 60 percent by weight of the composition of hydrogen peroxide at 20 volumes or equivalent quantities of another oxidizing agent, especially if it is desired to achieve a simultaneous bleaching of the fiber.

In another embodiment of the present invention, the novel diphenylamines can also be employed in the production of capillary hair-setting lotions. These lotions contain in dilute lower alkanol solution having a titer ranging from about 50° to 80° at least one cosmetic resin and at least one compound having the formula:

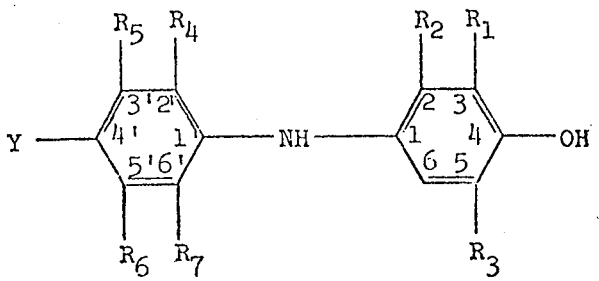

wherein Y, $R_1$, $R_2$, $R_3$, $R_4$, $R_5$, $R_6$ and $R_7$ have the meaning indicated above for the dyeing composition.

The cosmetic film-forming resin employed in the composition of this invention can be any of those conventionally employed in hair-setting lotions. Generally, such cosmetic film-forming resins have a molecular weight ranging from about 10,000 – 700,000, or even higher.

Representative cosmetic film-forming resins that can be employed include polyvinylpyrrolidone having a molecular weight of about 10,000 to 700,000; copolymer of vinylpyrrolidone and vinyl acetate, 70%–30% to 30%–70% having a molecular weight of 40,000 – 400,000; copolymer of vinyl acetate and an unsaturated carboxylic acid such as crotonic acid, 90% : 10%, having a molecular weight of 45,000 to 70,000; copolymer resulting from the polymerization of vinyl acetate (75–85%), crotonic acid (5–15%) and an acrylic or methacrylic ester (5–15%) or an alkylvinyl ether (5–15%); copolymer resulting from the copolymerization of vinyl acetate (63–88%), crotonic acid (5–15%) and (a) a vinyl ester of a long carbon chain acid having 10–22 carbon atoms or (b) an alkyl or methalkyl ester of a long carbon chain acid having 10–22 carbon atoms (5–25%); copolymer resulting from the copolymerization of an ester derived from an unsaturated alcohol having 2–12 carbon atoms and a saturated short chain carboxylic acid having 2–5 carbon atoms (65–80%) and an unsaturated acid having 4–20 carbon atoms (7–12%) and at least one ester derived from a saturated alcohol having 8–18 carbon atoms and an unsaturated acid having 4–20 carbon atoms (10–20%); a copolymer resulting from the polymerization of at least an unsaturated ester and at least an unsaturated acid; a copolymer of maleic anhydride and methyl vinyl ether in a molar ratio of, preferably 1:1 and having a specific viscosity between 0.1–3.5 when measured at 25°C and at a concentration of 1 g in 100 cc of methyl ethyl ketone; the monoethylester, monoisopropylester or monobutylester of said maleic anhydride and methyl vinyl ether copolymer and the monobutylester of a copolymer of maleic anhydride and butyl vinyl ester wherein the mole ratio of maleic anhydride to butyl vinyl ether is 1:1; terpolymers resulting from the polymerization of vinyl acetate (75–85%), alkyl stearate (10–20%) and alkoxy acetic acid (3–10%); terpolymers resulting from the polymerization of methyl methacrylate (15–25%), stearyl methacrylate (18–28%) and dimethyl methacrylate (52–62%). The cosmetic film-forming resin is generally used in amounts of about 1–3 percent by weight of said composition.

The alcohols suitable for making said hair-setting lotions are lower alkanols, preferably ethanol or isopropanol. These alcohols are used in a proportion of 20 to 50% by weight of the total composition.

The hair-setting lotions according to the invention contain from 0.01 to 0.2% by weight of the diphenylamine leucoderivatives defined above, and have a pH between 7 and 10, and preferably between 7 and 10. The pH can be obtained by adding to the lotion an alkaline agent such as ammonia or triethanolamine.

The hair-setting lotion according to the invention is employed in a conventional manner by applying the same to previously washed and rinsed wet hair followed by rolling the treated hair on curlers and thereafter drying it.

The hair-setting lotions of the present invention make it possible to impart to the hair a remarkable coloring characterized by its uniformity and its brightness, without it being necessary to take particular precautions and regardless of the degree of sensitivity of the hair being treated. In particular, in the case of irregularly bleached hair the hairsetting lotions of this invention make it possible to obtain results that are quite hard to achieve by standard dyeing processes.

The coloring of the hair obtained, in addition to its qualities of uniformity and brightness, is also characterized by glints which is an additional quality highly prized by hair dyers.

Further, the hair-setting lotions of the present invention can also contain known leucoderivatives, particularly leucoderivatives of indamines, indophenols and indoanilines.

The following examples are given to illustrate the present invention. Unless otherwise specified all parts and percentages are by weight.

EXAMPLE 1

3,5-dimethyl-4-hydroxy-4'-amino-3',5'-dimethyl-2'-methoxy diphenylamine is prepared according to the following reaction:

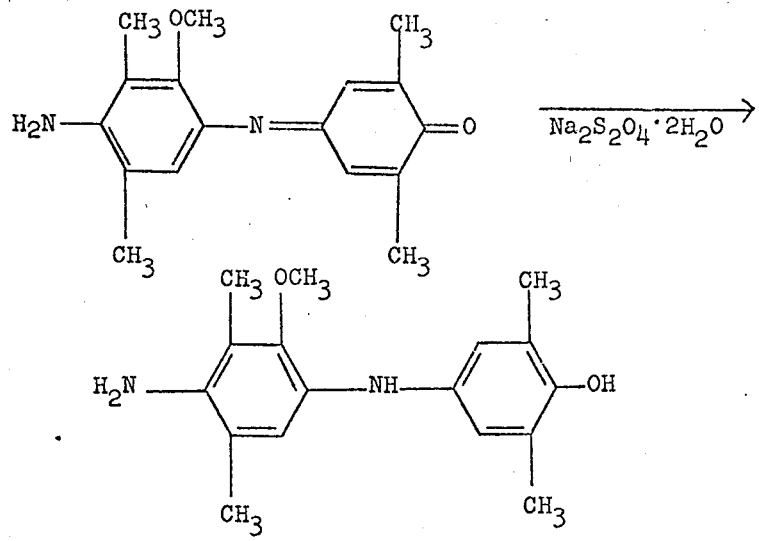

To 750 cm³ of a normal NaOH solution containing 73 g (0.35 mole) of sodium hyposulfite, there is added, little by little, with stirring and under a nitrogen atmosphere, 0.1 mole (28.4 g) of N-[(4'-amino-3',5'-dimethyl-2'-methoxy)phenyl]2,6-dimethyl-benzoquinoneimine in solution in 300 cm³ of ethyl alcohol, while keeping the temperature of the reaction mixture in the vicinity of 30°C. When the reduction reaction is completed the reaction mass is rapidly filtered. The filtrate is cooled and neutralized with acetic acid. 27 g of the above diphenylamine leucoderivative are filtered. After washing with water and drying under a vacuum, the said product exhibits a melting point of 137°C.

Molecular mass calculated for $C_{17}H_{22}N_2O_2$ = 286
Molecular mass found by potentiometric dosing in acetic acid by perchloric acid = 291.

| Analysis | Calculated for $C_{17}H_{22}N_2O_2$ | Found | |
|---|---|---|---|
| N% | 9.78 | 9.70 | 9.66 |

EXAMPLE 2

3,6-dimethyl-4-hydroxy-4'-amino-3',5'-dimethyl-2'-methoxy-diphenylamine is prepared according to the following reaction:

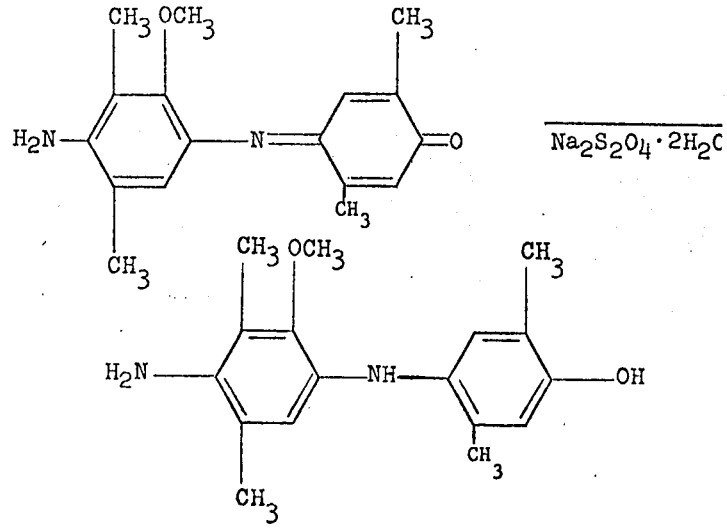

To 35 cm³ of a normal NaOH solution containing 3.5 g (0.016 mole) of sodium hyposulfite, there is added, with stirring and under a nitrogen atmosphere, 0.005 mole (1.42 g) of N-[(4'-amino-3',5'-dimethyl-2'-methoxy) phenyl]2,5-dimethyl-benzoquinoneimine in 15 cm³ of ethyl alcohol, while keeping the temperature of the reaction mixture in the vicinity of 30°C. When the reaction is finished, the mixture is neutralized with acetic acid and then filtered under a nitrogen atmosphere. 1.1 g of the above diphenylamine luecoderivative are obtained which, after washing in water and drying under a vacuum, exhibits a melting point of 110°C.

Molecular mass calculated for $C_{17}H_{22}N_2O_2 = 286$

Molecular mass found by potentiometric dosage in acetic acid by perchloric acid = 290.

| Analysis | Calculated for $C_{17}H_{22}N_2O_2$ | Found | |
|---|---|---|---|
| N% | 9.78 | 9.79 | 9.78 |

To 750 cm³ of a normal NaOH solution containing 0.47 mole (100 g) of sodium hyposulfite there is added, little by little, with stirring and under a nitrogen atmosphere, 0.2 mole (45.4 g) of N-[(4'-amino)phenyl]-5-amino-2-methyl-benzoquinoneimine in solution in 250 cm³ of ethyl alcohol, while keeping the temperature of the reaction mixture in the vicinity of 30°C. When the reduction is finished, acetic acid is added until a pH of about 7 is obtained. 44 g of the above diphenylamine leucoderivative are obtained and filtered under nitrogen. After washing the leucoderivative in water and drying it under a vacuum, it exhibited a melting point of 177°c.

Molecular mass calculated for $C_{13}H_{15}N_3O = 229$

Molecular mass found by potentiometric dosage in methylisobutylketone by perchloric acid = 224.

| Analysis | Calculated for $C_{13}H_{15}N_3O$ | Found | |
|---|---|---|---|
| N% | 18.34 | 18.62 | 18.42 |

EXAMPLE 3

2-amino-4-hydroxy-5-methyl-4'-amino-diphenylamine is prepared in accordance with the following reaction:

EXAMPLE 4

2-acetylamino-4-hydroxy-5-methyl-4'-amino-2'-methoxy-5'-methyl-diphenylamine is prepared in accordance with the following reaction:

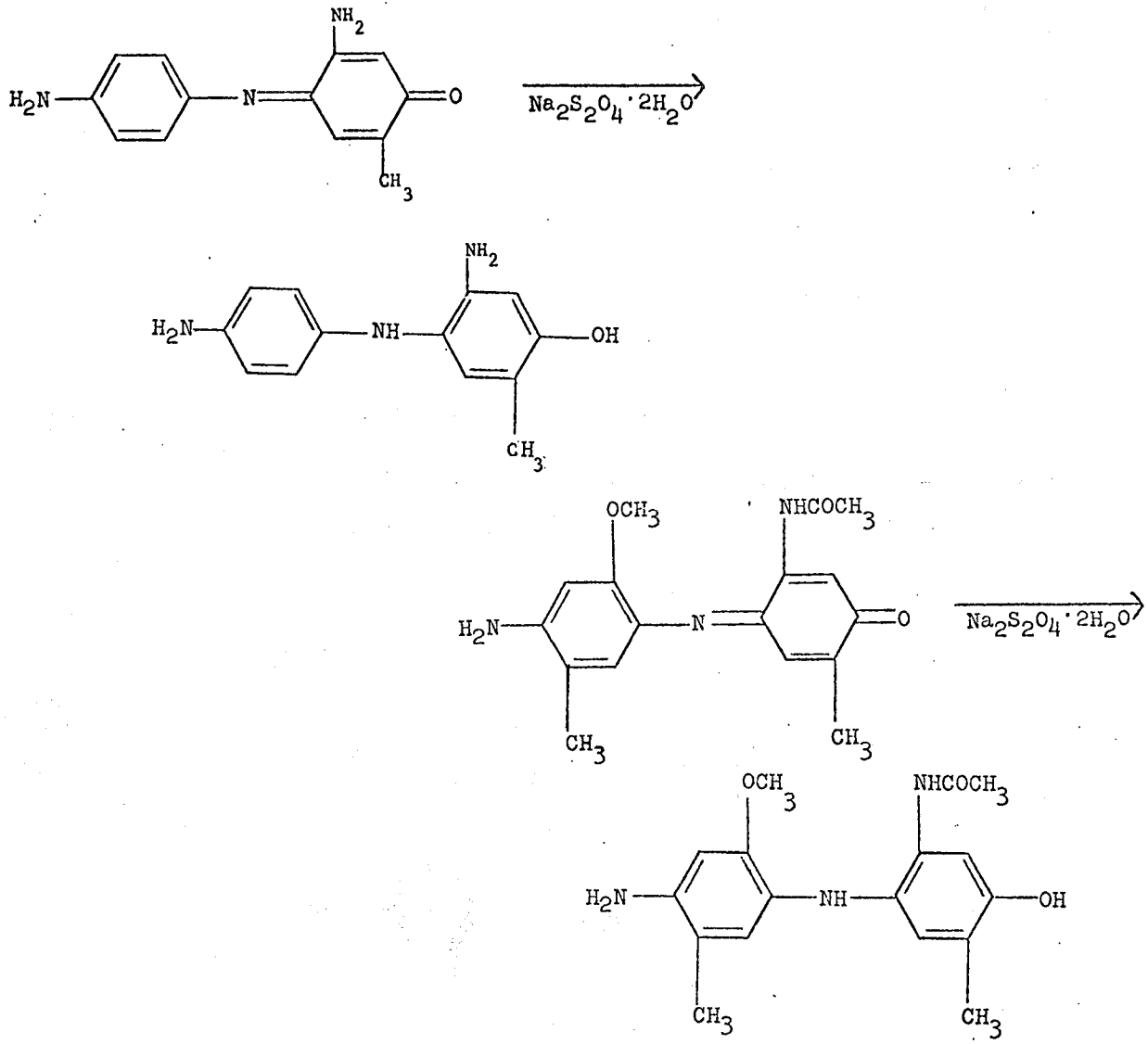

To 200 cm³ of a normal NaOH solution containing 0.1 mole (21 g) of sodium hyposulfite there is added, little by little, with stirring and under a nitrogen atmosphere, 0.032 mole (9.5 g) of N-[(4'-amino-2'-methoxy-5'-methyl)phenyl]3-acetylamino-6-methyl-benzoquinoneimine in solution in 50 cm³ of ethyl alcohol, while keeping the temperature of the reaction mixture in the vicinity of 30°C. When the reduction reaction is finished, acetic acid is added until a pH of about 7 is obtained. 8.8 g of the above diphenylamine leucoderivative are filtered. After washing in water and drying under a vacuum the said product exhibits a melting point of 233°C.

Molecular mass calculated for $C_{17}H_{21}N_3O_3 = 315$

Molecular mass found by potentiometric dosage in acetic medium by perchloric acid = 322.

| Analysis | Calculated for $C_{17}H_{21}N_3O_3$ | Found | |
|---|---|---|---|
| N% | 13.33 | 13.17 | 13.24 |

EXAMPLE 5

The monohydrochloride, monohydrate of 2-amino-4-hydroxy-5-methyl-4'-hydroxy-diphenylamine is prepared in accordance with the following reaction:

0.13 mole (30 g) of N-[(4'-hydroxy)phenyl] 5-amino-2-methyl-benzoquinoneimine is dissolved in a liter of 0.5N NaOH solution. Little by little, there is added thereto, with stirring and under a nitrogen atmosphere, 0.25 mole (52 g) of sodium hyposulfite, while keeping the temperature of the mixture in the vicinity of 30°C. When the reduction is finished, acetic acid is added until a pH close to neutrality is obtained. The resulting leucoderivative is filtered under nitrogen and is carefully washed with water. It is then converted into 2-amino-4-hydroxy-5-methyl-4'-hydroxy-diphenylamine monohydrochloride, monohydrate by treatment with 2N hydrochloric acid. This product, after recrystallization in water, melts with decomposition at 144°C.

Molecular mass calculated for $C_{13}H_{14}N_2O_2 \cdot HCl, H_2O = 284.5$

Molecular mass found by potentiometric dosage in an aqueous medium with a soda solution = 283.

EXAMPLE 6

2-amino-4-hydroxy-5-methyl-3',5'-dimethyl-4'-hydroxy-diphenylamine is prepared in accordance with the following reaction:

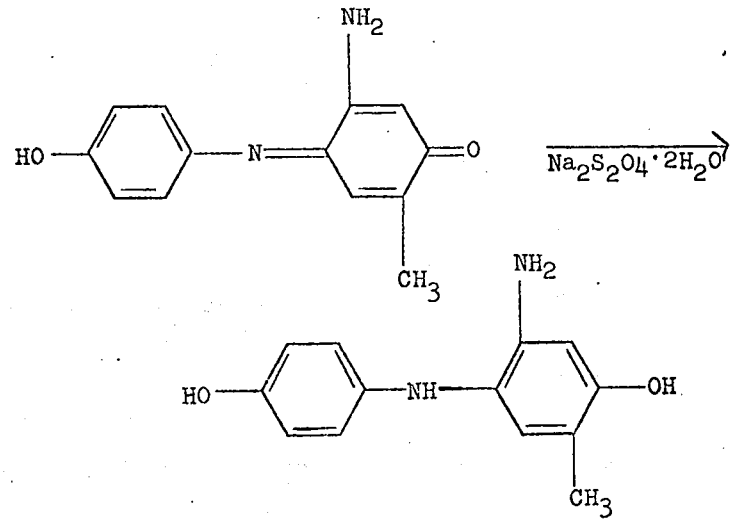

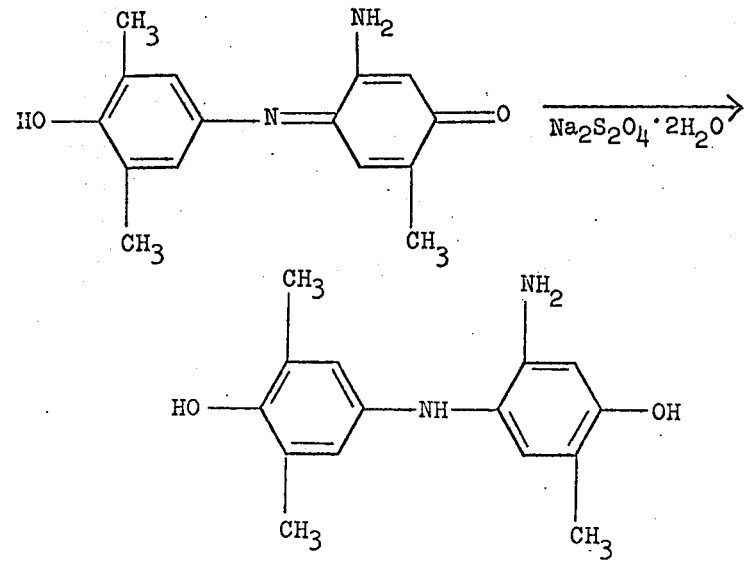

0.01 mole (2.56 g) of N-[4'-hydroxy-3',5'-dimethyl)-phenyl] 5-amino-2-methyl-benzoquinoneimine is dissolved in 75 cm³ of 0.5N NaOH solution. There is then added thereto, little by little, with stirring and under a nitrogen atmosphere, 0.02 mole (4.2 g) of sodium hyposulfite. When the reduction reaction is finished, acetic acid is added in amounts sufficient to lower the pH to about 6. The resulting above leucoderivative is filtered and washed with water and then dried under a vacuum. After recrystallization in benzene, it exhibited a melting point of 167°C.

Molecular mass calculated for $C_{15}H_{18}N_2O_3 = 258$

Molecular mass found by potentiometric dosage in methylisobutylketone by perchloric acid = 263.

| Analysis | Calculated for $C_{15}H_{18}N_2O_3$ | Found | |
|---|---|---|---|
| N% | 10.85 | 10.97 | 11.04 |

EXAMPLE 7

Preparation of 5-acetylamino-4-hydroxy-2-chloro-3',6'-dimethyl-4'-amino-diphenylamine of the formula

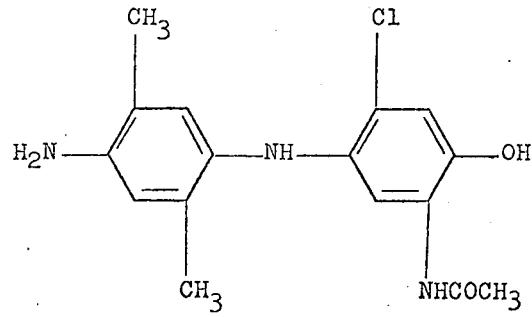

Step 1

Preparation of N-[(4'-amino-3',6'-dimethyl)-phenyl]-6-acetylamino-3-chloro-benzoquinoneimine of the formula

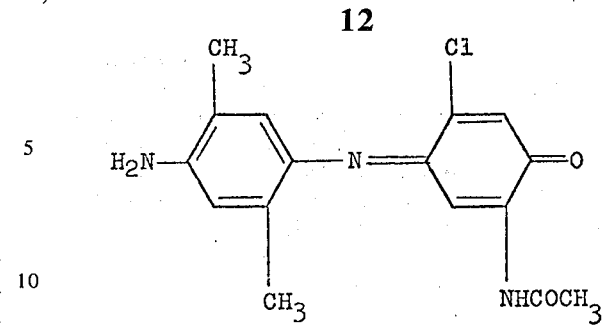

0.02 mole (3.71 g) of 2-acetylamino-5-chloro phenol is dissolved in 40 cc of acetone to which have been added 20 cc of water and 40 cc of ammonia, 22° Be. To this solution, cooled in ice, there are simultaneously added little by little, with agitation, and by means of two dropping funnels, on the one hand 0.02 mole (4.18 g) of 2,5-dimethyl paraphenylene diamine dihydrochloride in 40 cc of water, and on the other hand 0.04 mole (9.2 g) of ammonium persulfate in 40 cc of water. At the termination of the addition of these reactants, the above indoaniline, which has precipitated, is recovered from the reaction medium by filtering the same. The precipitate is then washed with water, recrystallized in a mixture of dimethyl formamide and water and dried under a vacuum. The resulting product melts at 240°C with decomposition.

| Analysis | Calculated for $C_{16}H_{16}N_3O_2Cl$ | Found | |
|---|---|---|---|
| C% | 60.47 | 60.41 | 60.20 |
| H% | 5.03 | 5.33 | 5.32 |
| N% | 13.22 | 13.23 | 13.07 |
| Cl% | 11.18 | 11.12 | 11.26 |

Step 2

Preparation of 5-acetylamino-4-hydroxy-2-chloro-3',6'-dimethyl-4'-amino-diphenylamine by the following reaction scheme:

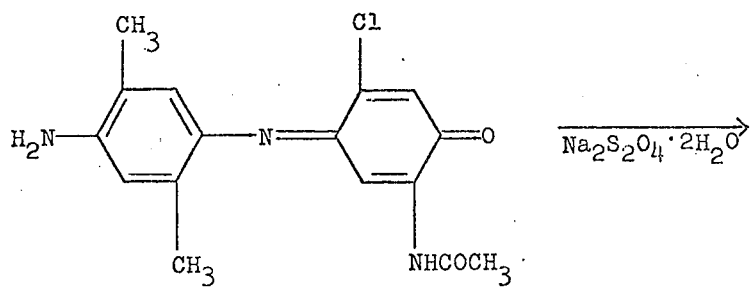

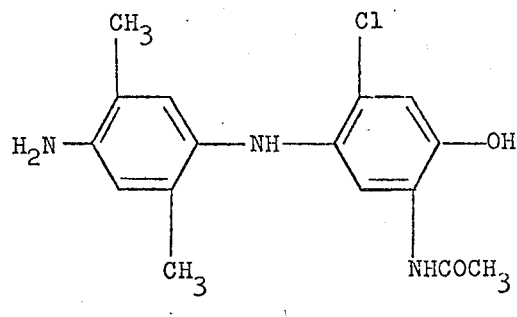

0.02 mole (4.2 g) of sodium hyposulfite is dissolved in 30 cc of a 1.5N NaOH solution to which have been added 10 cc of ethanol. To this solution, cooled in an ice bath, there is added little by little, with good agitation, 0.0063 mole (2 g) of N-[(4'-amino-3',6'-dimethyl) phenyl]-6-acetylamino-3-chloro-benzoquinoneimine. When the reduction is terminated the reaction medium has the color of light mahogany. Acetic acid is then added to adjust the pH thereof to 8 and to precipitate the above leucoderivative. The resulting precipitate is then filtered and washed first with distilled water and then with a 50% aqueous acetone solution. After drying under a vacuum, the product exhibits a melting point of 228°C.

| Analysis | Calculated for $C_{16}H_{18}N_3O_2Cl$ | Found | |
|---|---|---|---|
| C% | 60.09 | 60.37 | 60.43 |
| H% | 5.62 | 5.84 | 6.00 |
| N% | 13.14 | 12.92 | 13.02 |
| Cl% | 11.11 | 10.95 | 11.00 |

EXAMPLE 8

Preparation of 5,3',5'-trimethyl-4-trimethyl-4-hydroxy-2-acetylamino-4'-amino-diphenylamine in accordance with the following reaction scheme:

In one liter of a 1N NaOH solution there is dissolved 0.29 mole (67 g) of sodium hyposulfite. While maintaining this reaction medium at a temperature lower than 6°C, there is added, little by little, with agitation, 0.1 mole (29.7 g) of N-[(4'-amino-3',5'-dimethyl)-phenyl]-6-methyl-3-acetylamino-benzoquinoneimine, partially in solution in 200 cc of ethanol, 96° titer. When the reduction is terminated, the reaction medium has a very pale mahogany color. The reaction medium is then filtered to remove a small amount of insoluble product. To the resulting filtrate there is then added sufficient acetic acid to adjust the pH thereof to 7 and to precipitate the above substituted diphenylamine. The precipitate is then filtered, washed with water, recrystallized in a mixture of dimethyl formamide and water, and then dried under a vacuum. The thus recovered product exhibits a melting point of 252°C.

| Analysis | Calculated for $C_{17}H_{21}O_2N_3$ | Found | |
|---|---|---|---|
| C% | 68.23 | 68.36 | 67.94 |
| H% | 7.02 | 7.09 | 7.12 |
| N% | 14.05 | 13.98 | 14.03 |

EXAMPLE 9

Preparation of 5-methyl-2-acetylamino-4-hydroxy-2'-methoxy-4'-amino-diphenylamine in accordance with the following reaction scheme:

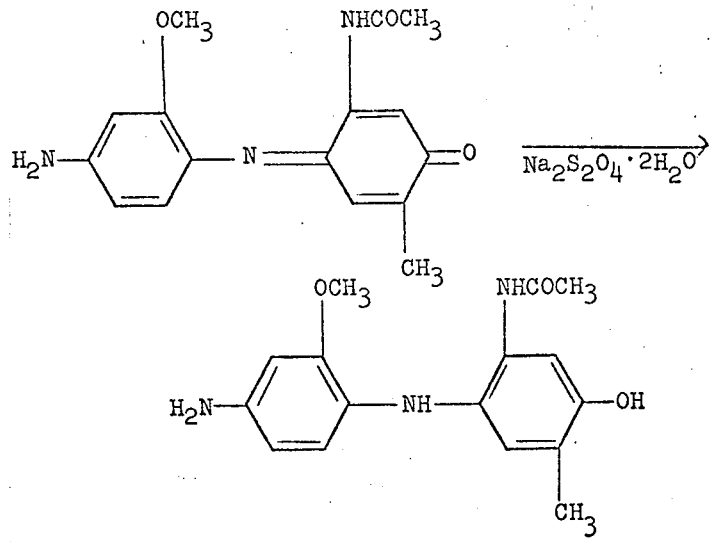

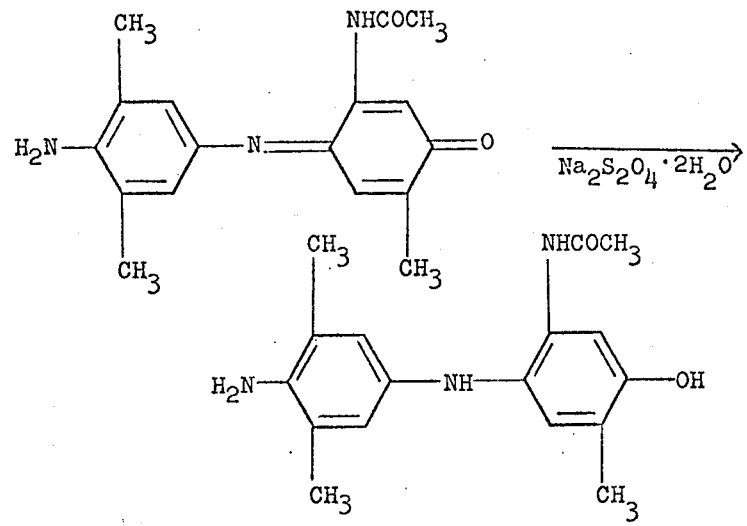

0.12 mole (26 g) of sodium hyposulfite is dissolved in 320 cc of 1N NaOH solution. To this solution there is added, little by little, with agitation and while maintaining the temperature of the reaction mixture at about 10°C, 0.04 mole (11.96 ) of N-[(4'-amino-2'-methoxy)phenyl]-6-methyl-3-acetylamino benzoquinoneimine, partially dissolved in 120 cc of ethanol. When the reduction is terminated, the reaction medium is colorless. There is then added thereto sufficient acetic acid to adjust its pH to 7 and to precipitate the above leucoderivative. The resulting precipitate is filtered, washed with water, recrystallized in a mixture of dimethyl formamide and water, and dried under a vacuum. The product exhibits a melting point of 220°C.

| Analysis | Calculated for $C_{16}H_{19}O_3N_3$ | Found | |
|---|---|---|---|
| C% | 63.79 | 63.64 | 63.68 |
| H% | 6.31 | 6.50 | 6.42 |
| N% | 13.95 | 13.96 | 14.01 |

EXAPLE 10

Preparation of 2,5-diacetylamino-4,4'-hydroxy-2'-chloro-diphenylamine in accordace with the following reaction scheme:

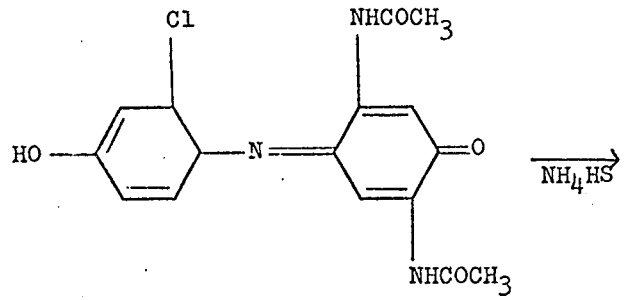

0.0025 mole (0.87 g) of N-[(4'-hydroxy-2'-chloro)-phenyl]-3,6diacetylamino benzoquinoneimine is partially dissolved in 20 cc of a 50% aqueous ethanolic solution. To the resulting reaction medium there is added, little by little, at ambient temperature and with agitation, an aqueous solution of ammonium hydrosulfide, previously prepared by saturating an aqueous ammonical solution, 19° Be, with hydrogen sulfide. This addition is continued until the reaction medium becomes colorless. The reaction medium is then diluted by the addition thereto of 30 cc of water to which is then added sufficient acetic acid to adjust the pH thereof to 7 and to precipitate the above diphenylamine. The precipitate is then filtered, washed with water and dried under a vacuum. It melts at 271°C.

| Analysis | Calculated for $C_{16}H_{16}N_3O_4Cl$ | Found | |
|---|---|---|---|
| C% | 54.93 | 54.72 | 54.67 |
| H% | 4.58 | 4.62 | 4.66 |
| N% | 12.01 | 11.98 | 11.89 |

EXAMPLE 11

Preparation of 3,5-dimethyl-4,4'-dihydroxy-2-acetylamino-diphenylamine in accordance with the following reaction scheme:

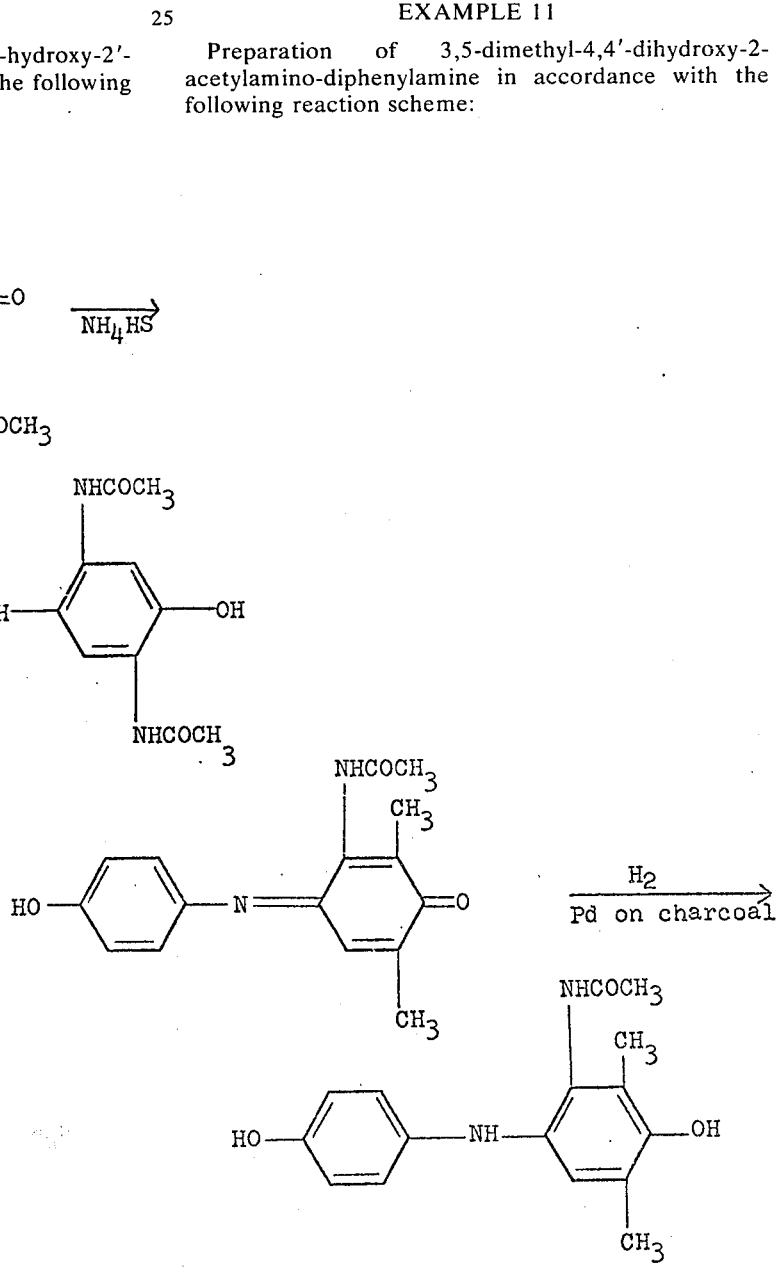

0.02 mole (5.66 g) of N-[(4'-hydroxy)phenyl]-2,6-dimethyl-3-acetylamino benzoquinoneimine is dissolved in 300 cc of absolute ethyl alcohol. The resulting solution is then catalytically hydrogenated, under atmospheric pressure, in the presence of Pd on charcoal (10% Pd on charcoal, manufactured by Englehard Industries). When the reduction is complete, the alcoholic solution is colorless. The reaction medium is then filtered to remove the catalyst. The alcohol is partially expelled by subjecting the reaction medium to a vacuum after which the above diphenylamine is precipitated by the addition of water thereto. The precipitate is filtered and dried under a vacuum. The product melts at 240°C.

| Analysis | Calculated for $C_{16}H_{18}N_2O_3$ | Found | |
|---|---|---|---|
| C% | 67.13 | 66.98 | 66.91 |
| H% | 6.29 | 6.34 | 6.35 |
| N% | 9.79 | 9.66 | 9.73 |

In 145 cc of 1.25N NaOH solution, 0.066 mole (14 g) of sodium hyposulfite is dissolved. To the resulting solution there is added, little by little, with agitation and while maintaining the temperature thereof at about 30°C, 0.02 mole (5.4 g) of N-[(4'-hydroxy)phenyl]-6-methyl-3-acetylamino benzoquinoneimine partially dissolved in 30 cc of ethanol. When the reduction is complete the reaction medium has a pale yellow color. To the reaction medium there is then added sufficient acetic acid to adjust the pH thereof to 7.5 and to precipitate the above substituted diphenylamine. The precipitate is then filtered, washed several times with water and dried under a vacuum. The product melts at 236°C.

| Analysis | Calculated for $C_{15}H_{16}O_3N_2$ | Found | |
|---|---|---|---|
| C% | 66.17 | 65.98 | 65.87 |
| H% | 5.93 | 5.96 | 6.01 |
| N% | 10.29 | 10.15 | 10.22 |

EXAMPLE 12

Preparation of 5-methyl-4-hydroxy-2-acetylamino-4'-hydroxy-diphenylamine in accordance with the following reaction scheme:

EXAMPLE 13

Preparation of 5-methyl-4-hydroxy-2-acetylamino-4'-amino-diphenylamine in accordance with the following reaction scheme:

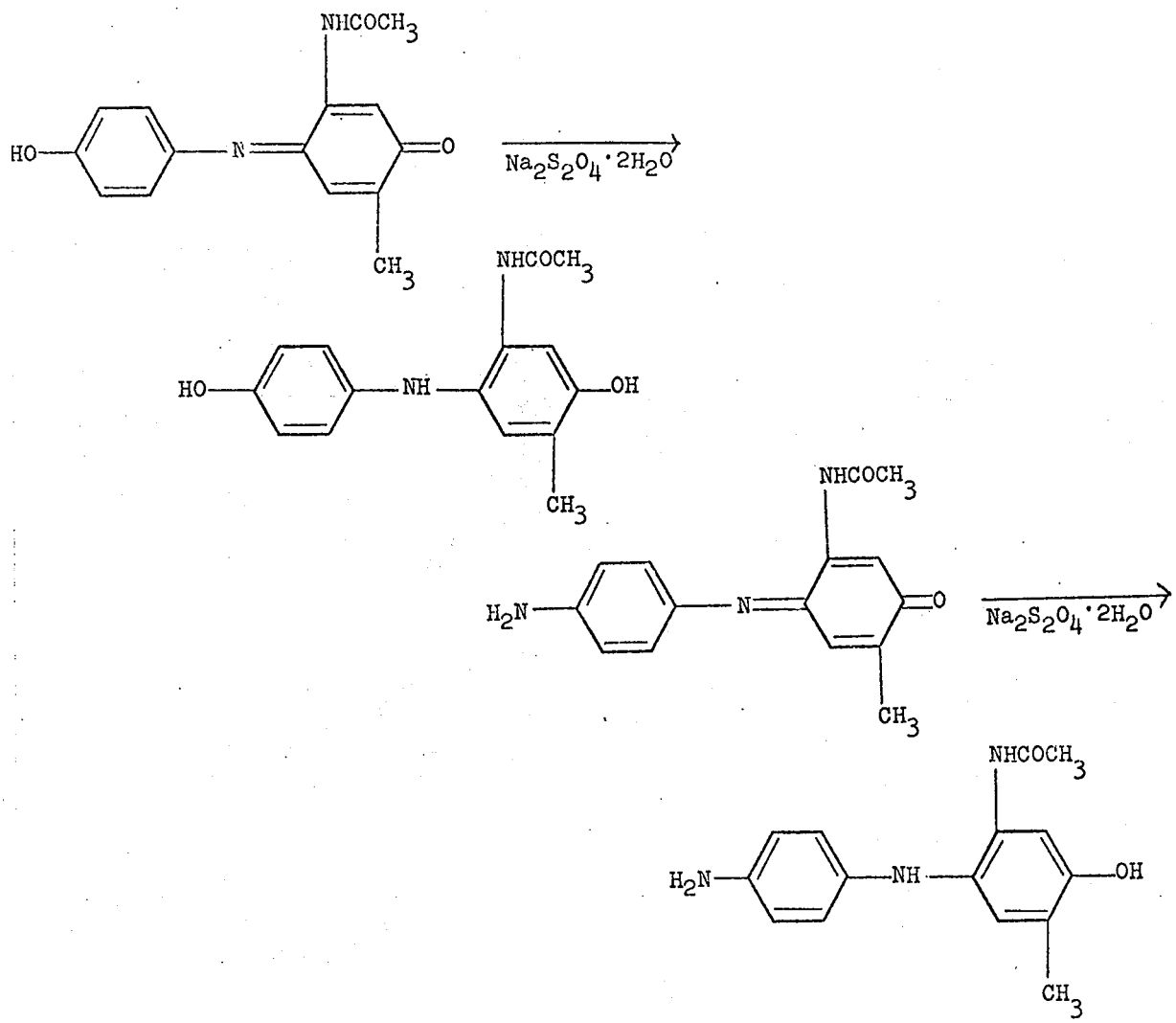

In 250 cc of a 1N NaOH solution, to which have been added 55 cc of ethyl alcohol, 95° titer, there is dissolved 0.117 mole (25 1 g) of sodium hyposulfite. There is then added to the resulting solution, little by little, with agitation and while maintaining the temperature thereof near 20°C, 0.045 mole (12.19 g) of N-[(4′-amino) phenyl]-6-methyl-3-acetylamino-benzoquinoneimine. When the reduction has terminated, there is added to the reaction medium sufficient acetic acid to adjust the pH thereto to 8 and to precipitate the above diphenylamine. The precipitate is then filtered, washed with water and recrystallized in a mixture of dimethyl formamide and water. After drying the same under a vacuum, it melts at 207°C.

| Analysis | Calculated for $C_{15}H_{17}N_3O_2$ | Found | |
|---|---|---|---|
| C% | 66.42 | 66.30 | 66.27 |
| H% | 6.27 | 6.34 | 6.32 |
| N% | 15.49 | 15.41 | 15.55 |

EXAMPLE 14

Preparation of 3,5-dimethyl-4-hydroxy-2-amino-3′-chloro-4′-amino diphenylamine in accordance with the following reaction scheme:

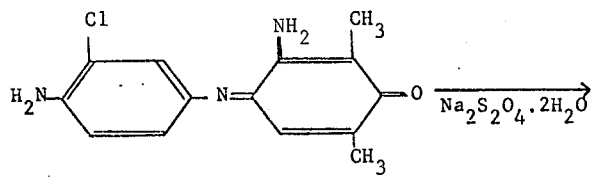

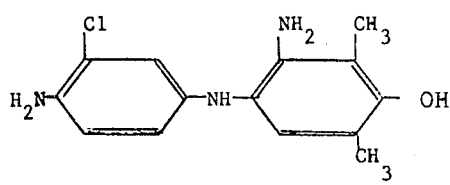

In 30 cc of a 1.25 NaOH solution, there is dissolved 0.015 mole (3.15 g) of sodium hyposulfite. There is then added to the resulting solution, little by little, with agitation 0.0036 mole (1 g) of N-[(4′-amino-3′-chloro) phenyl]-2,6-dimethyl-3-amino benzoquinone imine. At the end of the reduction the reaction medium has the color of light mahogany. It is cooled to about 0°C and sufficient acetic acid is then added to adjust the pH thereof to 6.5 in order to precipitate the above substituted diphenylamine. The precipitate is then filtered, washed with distilled water and dried under vacuum. The product melts at 110°C.

| Analysis | Calculated for $C_{14}H_{16}N_3$ ClO | Found | |
|---|---|---|---|
| C% | 60.54 | 60.69 | 60.72 |
| H% | 5.80 | 5.79 | 5.84 |
| N% | 15.13 | 15.62 | 15.15 |
| Cl% | 12.80 | 12.68 | 12.75 |

EXAMPLE 15

Preparation of a 5-methyl-4,4′-dihydroxy-2-ureido 2′-chloro diphenylamine

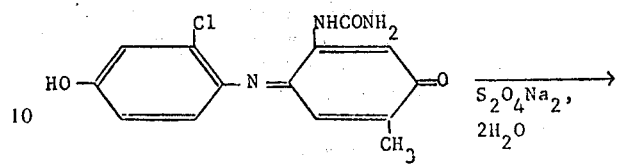

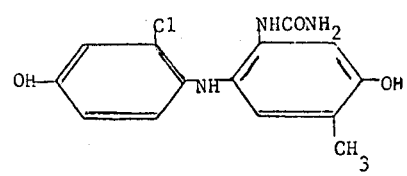

In 80 cc of a 1·N NaOH solution there is dissolved 0.04 mole (8.4 g) of sodium hyposulfite.

To the resulting solution there is added, little by little, with agitation while maintaining the temperature of the reaction medium near to 25°C, 0.01 mole (3.05 g) of N-[(4′-hydroxy-2′-chloro) phenyl]-6-methyl-3-ureido benzoquinone imine in 20 cc of ethanol. After the end of the addition the agitation is maintained during 15 minutes. The reaction medium is then cooled near to 0°C and sufficient acetic acid is added to adjust the pH thereof to 6.5 in order to precipitate the above substituted diphenylamine. The precipitate is then filtered, washed with distilled water and recrystallized in a mixture of dimethylformamide and water. After drying under vacuum at 60°C during 10 hours it melts at 250°C.

| Analysis | Calculated for $C_{14}H_{14}N_3 O_3$ Cl | Found | |
|---|---|---|---|
| C% | 54.64 | 54.12 | 54.26 |
| H% | 4.58 | 4.64 | 4.71 |
| N% | 13.65 | 13.75 | 13.57 |
| Cl% | 11.52 | 11.34 | 11.29 |

EXAMPLE 16

Preparation of a 5,3′-dimethyl-4-hydroxy-2-carbamylmethylamino-4′-amino diphenylamine

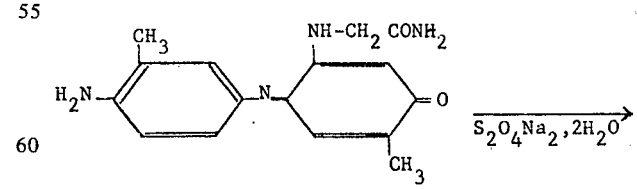

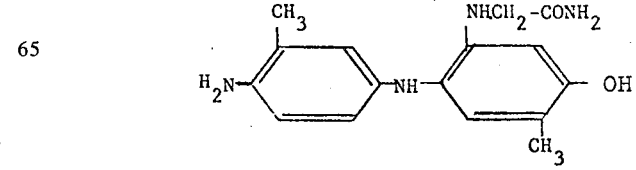

In 250 cc of 1 N NaOH solution there is added 0.09 mole (19 g) of sodium hyposulfite. To the resulting solution there is added, little by little, with agitation while maintaining the reaction medium near to 15°C, 0.03 mole (8.94 g) of N-[(4'-amino-3'-methyl) phenyl]-6-methyl-3-carbamylmethylamino benzoquinone imine in 150 cc of ethanol. At the end of the reduction the reaction medium is colorless. It is cooled to −10°C and sufficient acetic acid is added to adjust the pH thereof of 7 in order to precipitate the above substituted diphenylamine. The precipitate is filtered, washed with icy water and it is recrystallized in a mixture of dimethylformamide and water. After drying under vacuum it melts at 220°C.

| Analysis | Calculated for $C_{16}H_{20}N_4O_2$ | Found | |
|---|---|---|---|
| C% | 64.00 | 64.03 | 64.08 |
| H% | 6.66 | 6.67 | 6.61 |
| N% | 18.66 | 18.64 | 18.65 |

EXAMPLE 17

Preparation of 5-methyl-4,4'-dihydroxy-2-methylamino-3'-chloro diphenylamine:

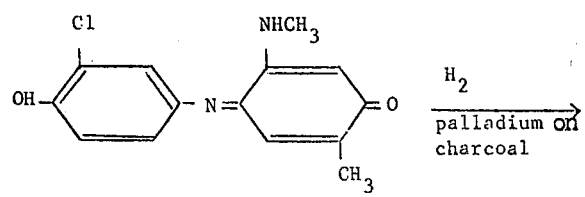

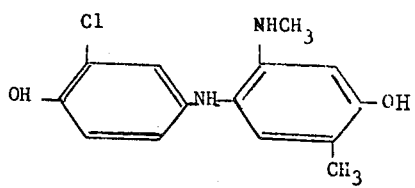

In 175 cc of absolute alcohol there is partially dissolved 0.02 mole (5.5g) of N-[(4'-hydroxy-3'-chloro) phenyl]-6-methyl-3-methylamino benzoquinone imine. The resulting solution is submitted to a catalytic hydrogenation at the ordinary pressure in presence of palladium on charcoal (10% Pd on charcoal, sold by Engelhard Industries). After 30 minutes there is no more hydrogen adsorption. The alcoholic solution which has the color of light mahogany is filtered in order to separate the catalyst. The alcohol is partially evaporated under vacuum until a volume of 30 cc. The above substituted diphenylamine is then precipitated by adding water. The precipitate is then filtered. After drying under vacuum it melts at 90°C.

| Analysis | Calculated for $C_{14}H_{15}N_2O_2Cl$ | Found | |
|---|---|---|---|
| C% | 60.33 | 59.92 | 59.98 |
| H% | 5.42 | 5.54 | 5.47 |
| N% | 10.05 | 10.08 | 10.08 |
| Cl% | 12.72 | 12.86 | 12.75 |

EXAMPLE 18

Preparation of a 3,5-dimethyl-2-ureido-4,4'-dihydroxy-'-chloro diphenylamine

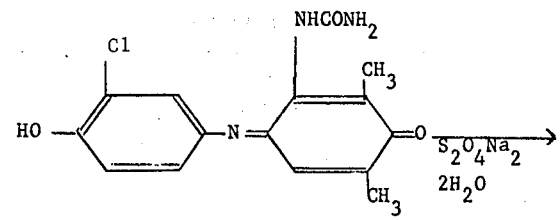

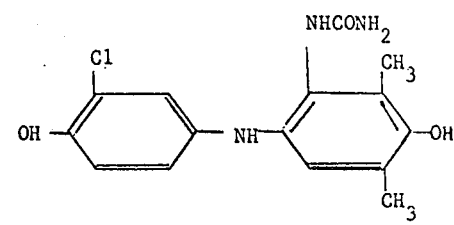

In 80 cc of a 1N NaOH solution there is dissolved to which there is added 20 cc ethanol there is dissolved 0.03 mole (6.3 g) of sodium hyposulfite. There is then added to the resulting solution, little by little, with agitation while maintaining the temperature of the reaction medium near to 25°C, 0.01 mole (3.19 g) of N-[(4'-hydroxy-3'-chloro) phenyl]-2,6-dimethyl-3-ureido benzoquinone imine. At the end of the reduction the color of the reaction medium is light mahogany. It is cooled near to 0°C and sufficient acetic acid is added to adjust the pH thereof to 6.5 in order to precipitate the above substituted diphenylamine. The precipitate is then filtered, washed with distilled water and recrystallized in a mixture of dimethylformamide and water. After drying under vacuum at 55°C it melts at 239°C.

| Analysis | Calculated for $C_{15}H_{16}N_3ClO_3$ | Found | |
|---|---|---|---|
| C% | 55.98 | 55.62 | 55.71 |
| H% | 4.97 | 5.02 | 5.04 |
| N% | 13.06 | 13.19 | 13.14 |
| Cl% | 11.04 | 10.94 | 10.98 |

EXAMPLE 19

Preparation of a 5,3'-dichloro-4,4'-dihydroxy-2-amino diphenylamine

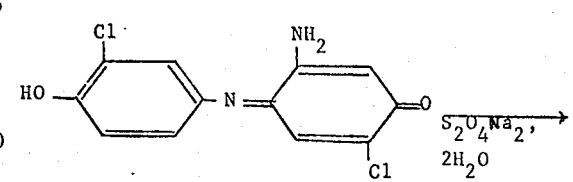

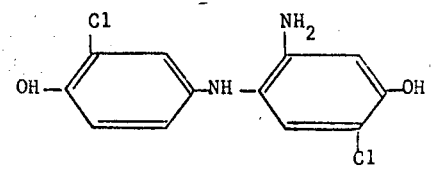

In 70 cc of 1,25 N NaOH solution to which 20 cc ethanol has been added there is dissolved 0.033 mole (7 g) of sodium hyposulfite. There is then added to the resulting solution, little by little, with agitation at room temperature 0.01 mole (2,83 g) of N-[(4'-hydroxy-3'-chloro) phenyl]-6-chloro-3-amino benzoquinone imine. At the end of the reduction the reaction medium is colorless. It is cooled near to 0°C and sufficient acetic acid is added to adjust the pH thereof to 6 in order to precipitate the above substituted diphenylamine. The precipitate is then filtered, washed with distilled water. After drying under vacuum at 50°C it melts at 189°C.

| Analysis | Calculated for $C_{12}H_{10}Cl_2N_2O_2$ | Found | |
|---|---|---|---|
| C% | 50.56 | 50.41 | 50.78 |
| H% | 3.53 | 3.62 | 3.74 |
| N% | 9.82 | 9.62 | 9.78 |
| Cl% | 24.91 | 24.64 | 24.76 |

EXAMPLE 20

Preparation of a 3,5-dimethyl-2-amino-4,4'-dihydroxy diphenylamine

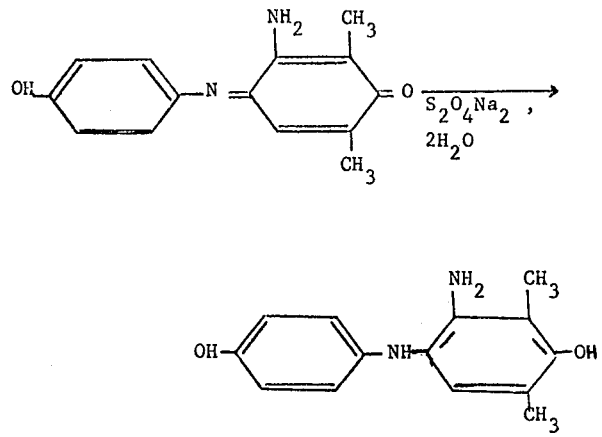

In 2500 cc of a 1 N NaOH solution there is dissolved 1.5 mole (320 g) of sodium hyposulfite.

There is then added to the resulting solution, little by little, with agitation while maintaining the temperature near to 20°C, 0.5 mole (121 g) of N-[(4'-hydroxy) phenyl]-2,6-dimethyl-3-amino benzoquinone imine in 600 cc of ethanol. At the end of the reduction the color of the reaction medium is light mahogany. It is cooled near to 0°C and sufficient acetic acid is added to adjust the pH thereof to 6.5 in order to precipitate the above substituted diphenylamine. The precipitate is filtered, carefully washed with distilled water. After drying under vacuum it melts at 180°C.

| Analysis | Calculated for $C_{14}H_{16}O_2N_2$ | Found | |
|---|---|---|---|
| C% | 68.83 | 68.24 | 68.32 |
| H% | 6.60 | 6.57 | 6.62 |
| N% | 11.47 | 11.40 | 11.39 |

The indophenols utilized in the present invention can be prepared by oxidizing in a first stage a paraamino phenol in an anhydrous solvent medium with an oxidizing agent present in amounts corresponding to 1 to 2 times, preferably 1.5 times the stoichiometric quantity for oxidizing the paraamino phenol, at a temperature between about 30° – 70°C to produce a quinoneimine, recovering the quninoneimine from the first stage reaction mass, condensing the thus recovered quinoneimine with a phenol in a molar ratio, preferably of 1:1, in a solvent such as water an preferably an aqueous ammoniacal solution or an inert organic solvent, at a temperature of about 5° – 30°C and recovering the thus produced indophenol. Conveniently, the anhydrous solvent employed in the first stage can be ethyl ether or isopropyl ether while the oxidizing agent can be silver oxide or lead oxide. Further, the quinoneimine can be recovered by filtering the first stage reaction mass and evaporating the resulting filtrate to dryness. Optionally, the thus recovered quinoneimine can be purified by recrystallizing the same from an anhydrous solvent selected from the group consisting of cyclohexane, benzene, hexane and mixtures thereof. The inert organic solvent employed in the condensation operation can be, for instance, ethyl ether or benzene.

Alternatively, the indophenol can be prepared by condensing a paraamino phenol on a phenol in an aqueous medium at a pH of about 8-12, preferably, about 10.5 to 11, at a temperature between 0°-40°C and in the presence of an oxidizing agent such as air, hydrogen peroxide, potassium or ammonium persulfate, sodium hypochlorite or potassium ferricyanide. The mole ratio of phenol to paraamino phenol ranges between about 0.5:1 and 2:1 and is preferably 1:1. The amount of oxidizing agent can vary between about 1 to 5 times the stoichiometric quantity for oxidizing the paraamino phenol to the corresponding quinoneimine. This amount is preferably 1 mole of persulfate or 2 moles of ferricyanide for 1 mole of paraamino phenol.

Yet another method of producing the indophenol involves condensing a chlorinated quinoneimine on a phenol, the condensation reaction being performed in an alkaline medium at a pH of about 10 to 12 and at a temperature of about 10°-40C. The mole ratio of chlorinated quinoneimine to phenol is preferably 1:1.

The indoanilines utilized in the present invention can be prepared by oxidizing in a first stage a paraphenylene diamine in an anhydrous solvent medium with an oxidizing agent present in amounts ranging between 1.5–2 moles per mole of paraphenylene diamine, at a temperature between about 30°-70°C to produce a quinonediimine recovering the quinonediimine from the first stage reaction mass, condensing the thus recovered quinonediimine with a phenol in a molar ratio of, for instance, 1:1, in a solvent such as an aqueous medium preferably an aqueous ammonical solution or an inert organic medium at a temperature of about 10°-40°C and recovering the thus produced indoaniline. The anhydrous solvent employed in the first stage can be ethyl ether or isopropyl ether while the oxidizing agent can be silver oxide or lead oxide. The quinoneimine can be recovered by filtering the first stage reaction mass and evaporating the resulting filtrate to dryness. Optionally, the thus recovered quinonediimine can be purified by recrystallizing the same from an anhydrous solvent such as cyclohexane, benzene, hexane and mixtures thereof. The inert organic medium employed in the condensation operation can be, for instance, ethyl ether or benzene.

Alternatively, the indoaniline can be prepared by condensing a paraphenylene diamine with a phenol in an aqueous medium having a pH of about 8-11 in the presence of an oxidizing agent and at a temperature between 0°-40°C. The oxidizing agent can be, for instance, hydrogen peroxide, ammonium persulfate, potassium persulfate, potassium ferricyanide, sodium hypochlorite or air present in amount of about 1 to 5 times the stoichiometric quantity Generally, the mole ratio of paraphenylene diamine to phenol ranges between 3-1 : 1 and is preferably 1 : 1.

A first solution is prepared by dissolving 0.05 mole (14.34 g) 2,6-dimethyl-3-methoxy paraphenylene diamine dihydrochloride in 500 cc of a 0.2 N NaOH solution. A second solution is prepared by dissolving 0.05 mole (7.32 g) 2,6-xylenol in 500 cc of a 0.2N NaOH solution. The two solutions are then mixed and to the resulting mixture there is slowly added, with agitation, 0.05 mole (13.40 g) potassium persulfate 13.50 in 500 cc water. When the addition is finished, the reaction mixture is allowed to stand for 1 hour at 0°. The above-identified indoaniline is then recovered by filtering the reaction mass on a suction filter, the yield amounting to 10.6 g. After recrystallization in an acetone-water mixture, the said indoaniline recovered melts at 123°.

| Analysis | Calculated for $C_{17}H_{20}N_2O_2$ | Found | |
|---|---|---|---|
| C% | 71.83 | 72.04 | |
| H% | 7.04 | 6.99 | |
| N% | 9.85 | 9.91 | 10.10 |

EXAMPLE 21

The N-[(4'-amino-3',5'-dimethyl-2'-methoxy) phenyl]-2,6-dimethyl-benzoquinone imine of example 1 is prepared in accordance with the following reaction:

EXAMPLE 22

The N-[(4'-amino-3',5'-dimethyl-2'-methoxy)-phenyl]2,5-dimethyl-benzoquinoneimine of Example 2 is prepared in accordance with the following reaction:

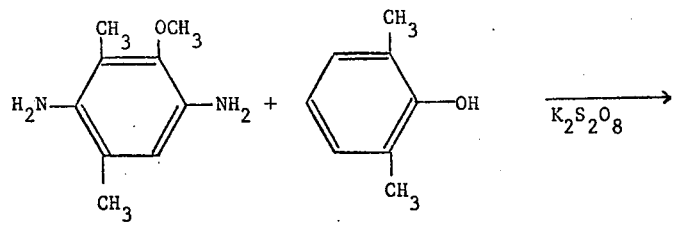

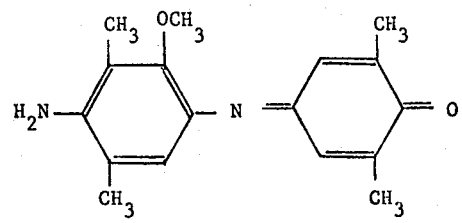

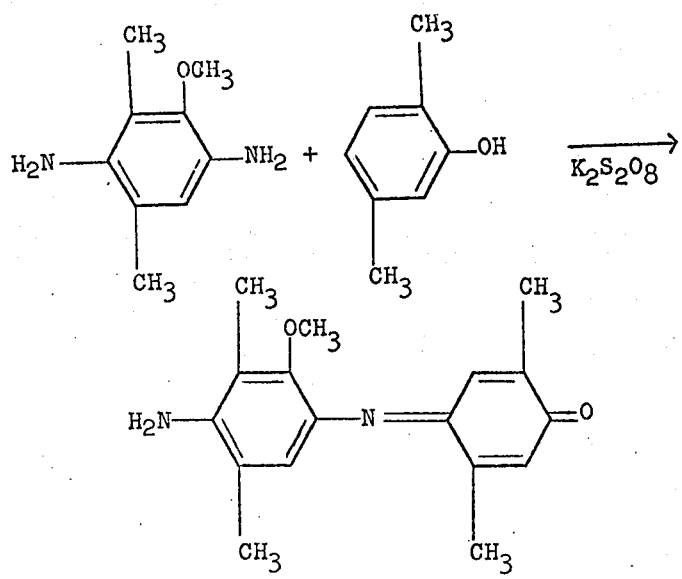

A first solution is prepared by dissolving 0.06 mole (14.34 g) 2,6-dimethyl 3-methoxy-paraphenylenediamine dihydrochloride in 600 cc of a 0.2N NaOH solution. A second solution is prepared by dissolving 0.06 mole (7.32 g) 2,5-xylenol in 600 cc of a 0.2N NaOH solution. These two solutions are mixed and there is then slowly added thereto, with agitation, a solution of 0.06 mole (16.20 g) potassium persulfate in 600 cc water. When the addition is completed, the resulting mixture is allowed to stand for one hour at ambient temperature and then the 9.1 g indoaniline are separated by filtering the reaction mass on a suction filter. After recrystallization in a dimethyl formamide and water mixture, the said indoaniline exhibited a melting point of 124°.

| Analysis | Calculated for $C_{17}H_{20}N_2O_2$ | Found | |
|---|---|---|---|
| C% | 71.83 | 72.03 | |
| H% | 7.04 | 7.04 | |
| N% | 9.85 | 9.55 | 9.75 |

EXAMPLE 23

The N-[(4'-amino)phenyl]-5-amino-2-methyl-benzoquinoneimine of Example 3 is prepared in accordance with the following reaction:

To a solution of 0.03 mole (5.44 g) paraphenylenediamine dihydrochloride dissolved in 100 cc water, ammonia is added in amounts sufficient to adjust the pH thereof to 8. This solution is immediately added to a solution of 0.01 mole (1.23 g) 5-amino-2-methyl phenol in 100 cc water. 30 cc ammonia 22° Be and 150 cc hydrogen peroxide to make 20 volumes are then added to this mixture which is then allowed to stand for 10 hours at room temperature. 2 g of the said indoaniline in crystalline form is recovered by filtering the reaction mass on a suction filter. After washing with water and acetone and recrystallizing the same from a dimethylformamide and water mixture, the resulting indoaniline had a melting point of 236°.

| Analysis | Calculated for $C_{13}H_{13}N_3O$ | Found | |
|---|---|---|---|
| C% | 68.72 | 68.65 | 68.51 |
| H% | 5.72 | 5.93 | 5.74 |
| N% | 18.50 | 18.29 | 18.25 |

EXAMPLE 24

The N-[(4'-amino-2'-methoxy-5'-methyl)phenyl] 3-acetylamino-6-methyl benzoquinoneimine of Example 4 is prepared in accordance with the following reaction:

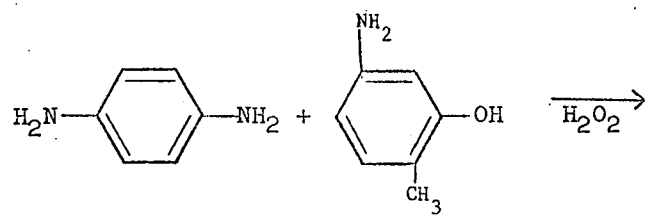

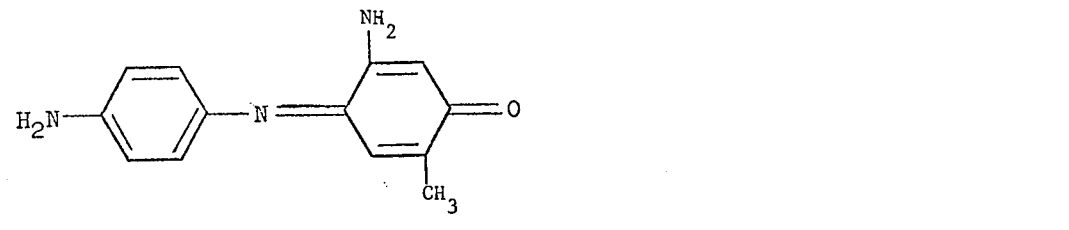

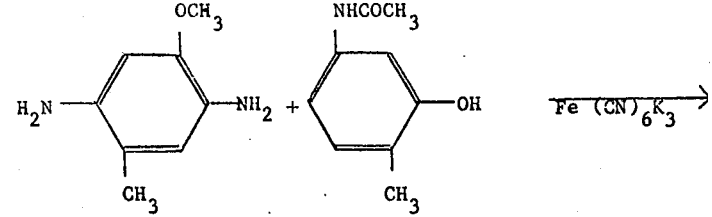

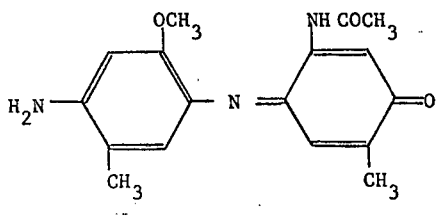

To a solution of 0.02 mole (4.5 g) 2-methoxy-5-methyl paraphenylene diamine dichlorhydrate in 200 cc water, there is added 10 cc ammonia 22°Be and then 0.02 mole (3.30 g) 5-acetylamino-2-methyl phenol, previously dissolved in 200 cc iced water to which 60 cc ammonia 22° Be has been added. Into the resulting mixture there is introduced, little by little, with agitation, a solution of 0.04 mole (13.1 g) potassium ferricyanide in 250 cc water. After one hour of agitation, the reaction mixture is filtered off and 5.4 g of said indoaniline is recovered which, after crystallization from ethyl acetate, exhibited a melting point of 220°C.

| | Calculated for | |
|---|---|---|
| Molecular weight calculated for $C_{17}H_{19}N_3O_2$ | | 313 |
| Molecular weight found by potentiometric determination effected with perchloric acid in acetic medium | | 316 |
| Analysis | Calculated for $C_{17}H_{19}N_3O_2$ | Found |
| N% | 13.40 | 13.33    13.42 |

EXAMPLE 25

The N-[(4'-hydroxy)phenyl] 5-amino-2-methyl benzoquinoneimine of Example 5 is prepared in accordance with the following reaction:

0.01 mole (1.09 g) of paraaminophenol is dissolved in 100 cm³ of a 0.1 N NaOH solution. A second solution of 0.01 mole (1.23 g) of 5-amino-2-methyl phenol in 100 cm³ of a 0.1N NaOH solution is also prepared. The two solutions are then mixed and air is bubbled in the resulting mixture for about 5 hours at ambient temperature. The reaction medium is then acidified with sufficient HCl to pH 5 to produce 1.2 g of said indophenol which is then filtered off and which, after recrystallization from a dimethylformamide-water mixture, melts at 215°.

| Analysis | Calculated for $C_{13}H_{12}N_2O_2$ | Found | |
|---|---|---|---|
| C% | 68.41 | 68.14 | 67.93 |
| H% | 5.26 | 5.25 | 5.26 |
| N% | 12.28 | 12.32 | |

EXAMPLE 26

The N[('-hydroxy-3',5'-dimethyl)phenyl]-5-amino-2-methyl benzoquinoneimine of Example 6 is prepared

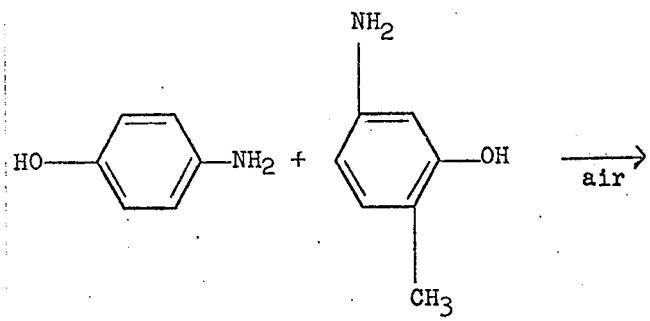

in accordance with the following reaction:

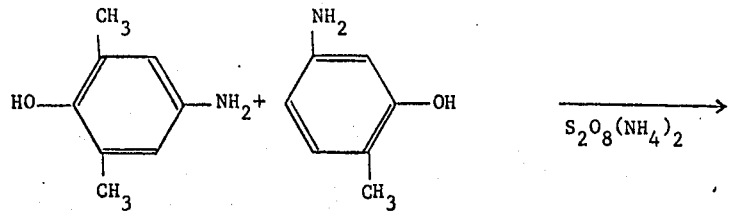

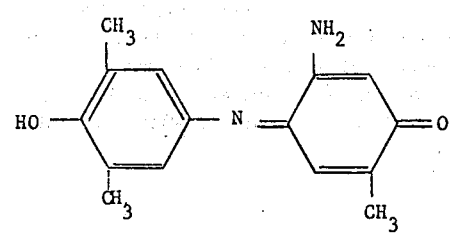

0.02 mole (2.46 g) of 2-methyl-5-amino phenol and 0.02 mole (3.83 g) of the monohydrate of 2,6-dimethyl-paraaminophenol HCl are dissolved in 200 cc of water to which has been added 80 cc of ammonia (22°Be). To this solution there is added, little by little, with agitation, 0.02 mole (4.56 g) of ammonium persulfate in solution in 50 cc of water. The resulting reaction mixture is then left to stand for 15 minutes at ambient temperature. There is then added sufficient acetic acid to adjust the pH thereof to about 7.5. 3.20 g of the above indophenol are recovered by filtering. After washing with water and with acetone, the chromatographically pure indophenol exhibits a melting point of 262°C.

| Molecular weight calculated for $C_{15}H_{16}N_2O_2$ | | 256 |
| Molecular weight found by potentiometric dosing in acetic acid with perchloric acid | | 257. |
| Analysis | Calculated for $C_{15}H_{16}N_2O_2$ | Found |
| --- | --- | --- |
| C% | 70.40 | 69.92 70.03 |
| H% | 6.25 | 6.19 6.37 |
| N% | 10.93 | 10.68 10.66 |

EXAMPLE 27

The N-[(4'-amino-3',5'-dimethyl) phenyl]-6-methyl-3-acetylamino benzoquinoneimine of example 8 is prepared in accordance with the following reaction scheme:

0.03 mole (6.27 g) 2,6-dimethyl-paraphenylene diamine on one hand and 0.027 mole 6-methyl-3-acetylamino phenol on the other hand are dissolved in 525 cc water to which 120 cc isopropylic alcohol and 135 cc ammonia 22° Be have been added. 0.06 mole (14.04 g) ammonium persulfate 97.5% dissolved in 60 cc water are added, little by little, while stirring to that solution cooled to 0°C. After the end of addition stirring is continued during 15 minutes after which the above crystallized benzoquinone imine is filtered. After washing with distilled water and drying the said benzoquinone imine is chromatographically pure and melts at 231°C.

| Analysis | Calculated for $C_{17}H_{19}N_3O_2$ | Found | |
| --- | --- | --- | --- |
| C% | 68.66 | 68.92 | 68.84 |
| H% | 6.44 | 6.43 | 6.37 |
| N% | 14.13 | 14.02 | 14.08 |

EXAMPLE 28

The N-[(4'-amino-2'-methoxy) phenyl]-6-methyl-3-acetylamino benzoquinone imine of example 9 is prepared in accordance with the following reaction:

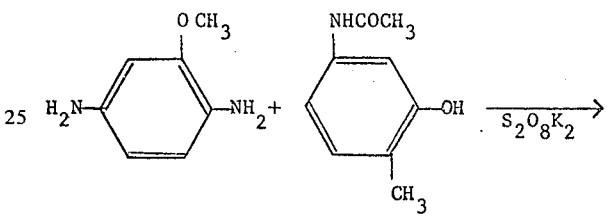

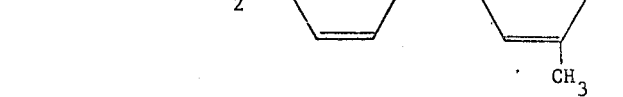

A first solution is prepared by dissolving 0.02 mole (4.22 g) 2,5-diamino anisole dichlorhydrate in 200 N NaOH solution. A second solution is prepared by dissolving 0.02 mole (3.3 g) 5-acetylamino-2-methyl phenol in 200 cc of a 0.2 N NaOH solution. The two solutions are mixed and there is then slowly added, with agitation, 0.02 mole (5.4 g) potassium persulfate, previously dissolved in 250 cc water. When the addition is completed, the reaction mixture is filtered off and 3.1 g of said indoaniline is recovered, which, after recrystallization from a mixture of dimethylformamide and water, exhibited a melting point of 215°C.

| Analysis | Calculated for $C_{16}H_{17}O_3N_3$ | Found | |
| --- | --- | --- | --- |
| C% | 64.21 | 64.45 | 64.16 |
| H% | 5.68 | 5.90 | 5.82 |
| N% | 14.04 | 14.30 | 14.12 |

EXAMPLE 29

The N-[(4'-hydroxy-2'-chloro) phenyl]-3,6-diacetylamino benzoquinone imine of example 10 is prepared in accordance with the following reaction:

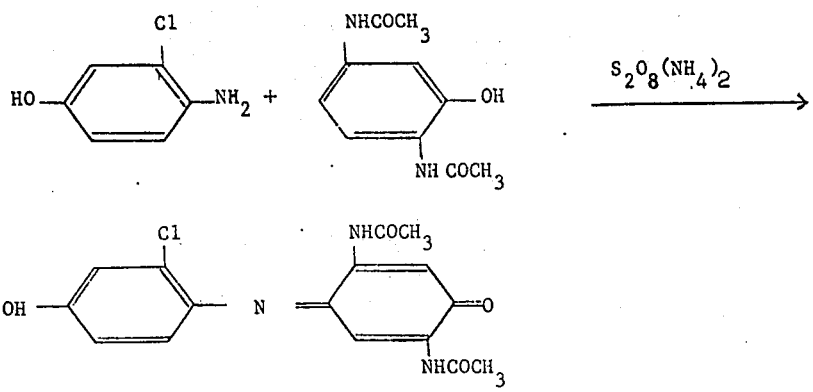

There is dissolved 0.01 mole (2.08 g) of 2,5-diacetamino phenol in 15 cc of acetone to which has been added 10 cc of ammonia (22°Be). There is then dissolved 0.01 mole (1.80 g) of 3-chloro-4-amino phenol monohydrochloride in 15 cc of water to which has been added 10 cc of acetone. The two solutions are mixed together and while maintaining the temperature at about 0°C, there is added thereto, with agitation, 0.02 mole (4.6 g) of ammonium persulfate in 25 cc of water. At the end of this addition step, the reaction mixture is filtered to recover the above indophenol. The thus recovered indophenol is washed, with good agitation, in water to which is added during the washing operation, sufficient acetic acid to maintain the pH of the wash medium at 6. Thereafter the wash medium is filtered to recover the indophenol which is then washed with water and recrystallized from a mixture of dimethylformamide and water. The product is then dried under a vacuum and is found to melt with decomposition above 270°C.

| Analysis | Calculated for $C_{16}H_{14}N_3ClO_4$ | Found | |
|---|---|---|---|
| C% | 55.24 | 54.97 | 54.83 |
| H% | 4.02 | 4.12 | 4.24 |
| N% | 12.08 | 11.98 | 12.06 |
| Cl% | 10.21 | 10.16 | 9.98 |

EXAMPLE 30

The N-[(4'-hydroxy) phenyl]-2,6-dimethyl-3-acetylamino benzoquinone imine of example 11 is prepared in accordance with the following reaction:

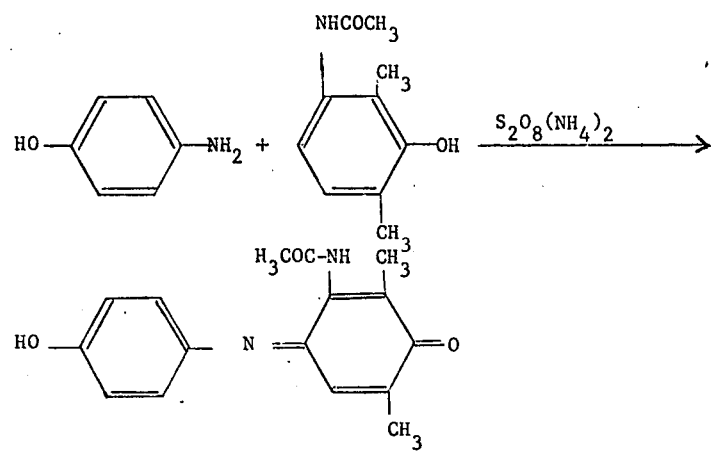

0.05 mole (5.45 g) of p-aminophenol and 0.05 mole (9 g) of 2,6-dimethyl-3-acetylamino phenol are dissolved in 100 cc of water, 50 cc of acetone and 25 cc of ammonia (22°Be). To this resulting solution, cooled in an ice bath, there is added, little by little, with agitation, 0.05 mole of ammonium persulfate in 25 cc of water. The reaction mixture is left to stand for 20 minutes at ambient temperature. Then, 6,7 g of the above indophenol are recovered by filtering. The indophenol after recrystallization from a mixture of acetone and water exhibits a melting point of 202°C.

| Molecular weight calculated for $C_{16}H_{16}N_2O_3$ | | 284 |
|---|---|---|
| Molecular weight found by potentiometric dosing in acetic acid by perchloric acid | | 288. |
| Analysis | Calculated for $C_{16}H_{16}N_2O_3$ | Found |
| C% | 67.60 | 66.92 67.20 |
| H% | 5.63 | 5.74 5.57 |
| N% | 9.85 | 9.75 9.72 |

EXAMPLE 31

The N-[(4'-hydroxy) phenyl]-6-methyl-3-acetylamino benzoquinone imine of example 12 is prepared in accordance with the following reaction:

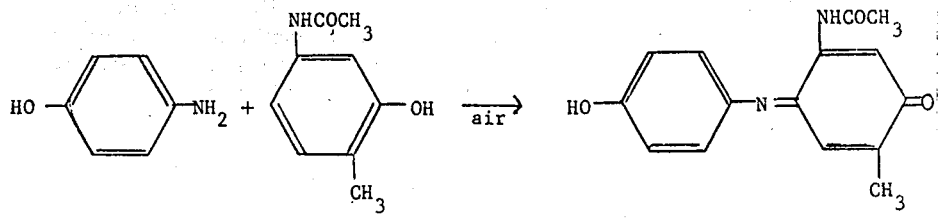

A first solution is prepared by dissolving 0.1 mole (16.5 g) of methyl-2 acetylamino-5 phenol in 500 cm³ of a frozen 0.2 N NaOH solution. A second solution is prepared by dissolving 0.1 mole (10.9 g) of paraaminophenol also in 500 cm³ of a frozen 0.2 N NaOH solution. The two solutions are mixed and, while the temperature is kept in the vicinity of 0°, air is bubbled for 5 hours through the resulting reaction mass. 20 g of said indophenol is recovered and is acidified with 20 cm³ of acetic acid and dried. After recrystallization in a dimethylformamide-water mixture, the purified indophenol melts at 254°C.

| Analysis | Calculated for $C_{15}H_{15}N_3O_2$ | Found | |
|---|---|---|---|
| C% | 66.91 | 66.11 | |
| H% | 5.57 | 5.75 | |
| N% | 15.61 | 15.52 | 15.47 |

EXAMPLE 33

The N-[(4'-amino-3'-chloro) phenyl]-3-amino-2,6-dimethyl benzoquinone imine of example 14 is prepared in accordance with the following reaction:

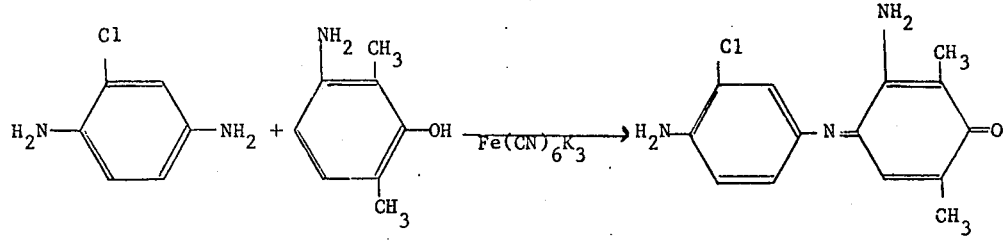

| Analysis | Calculated for $C_{15}H_{14}N_2O_3$ | Found |
|---|---|---|
| C% | 66.66 | 66.62 |
| H% | 5.18 | 5.21 |
| N% | 10.37 | 10.40 |

EXAMPLE 32

The N-[(4'-amino) phenyl]-6-methyl-3-acetylamino benzoquinone imine of example 13 is prepared in accordance with the following reaction:

0.02 mole (2.74 g) 3-amino-2,6-dimethyl phenol and 0.02 mole (2.85 g) chloroparaphenylenediamine are dissolved in 200 cc water to which there has been added 50 cc ammonia 22°Be. Little by little, there is added to this mixture, with agitation, 0.04 mole (13.6 g) potassium ferricyanide. When the addition is completed, 5 g of the above indoaniline is recovered by filtering the reaction mixture on a suction filter. The indoaniline is then washed with water and after recrystallization from a mixture of dimethylformamide and water, the product exhibited a melting point of 196°C.

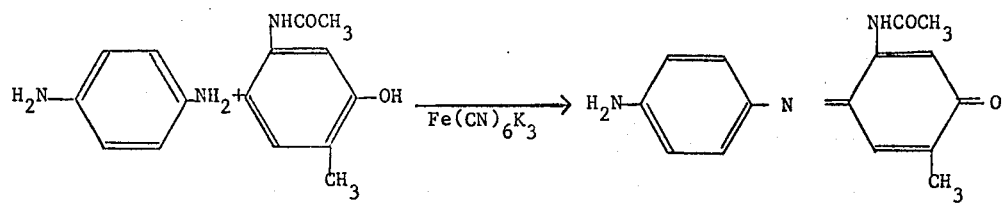

0.1 mole (18.1 g) paraphenylenediamine dichlorhydrate is dissolved in 100 cc water and the solution is made alkaline by use of 50 cc ammonia 22°Be. This solution is immediately added to 0.1 mole (16.5 g) 5-acetylamino-2-methyl phenol, previously dissolved in one liter of iced water to which 300 cc ammonia 22° Be has been added. Little by little, there is added to this mixture, with agitation, 0.2 mole (65.8 g) potassium ferricyanide dissolved in 1250 cc water. When this addition is completed, 16 g of the above indoaniline is recovered by filtering the reaction mixture on a suction filter. After washing with acetone and recrystallization froma dimethylformamide and water mixture, this indoaniline exhibited a melting point of 105°C.

| Analysis | Calculated for $C_{14}H_{14}O\ N_3Cl$ | Found | |
|---|---|---|---|
| C% | 60.98 | 60.51 | 60.61 |
| H% | 5.08 | 5.17 | 5.30 |
| N% | 15.24 | 15.17 | 14.95 |
| Cl% | 12.88 | 12.99 | 12.88 |

EXAMPLE 34

The N-[(4'-hydroxy-3'-chloro) phenyl]-3-methylamino-6-methyl benzoquinone imine of example 17 is prepared in accordance with the following reaction scheme:

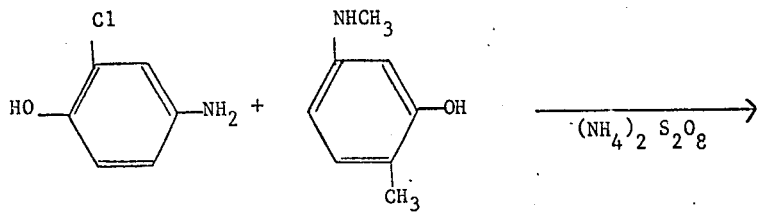

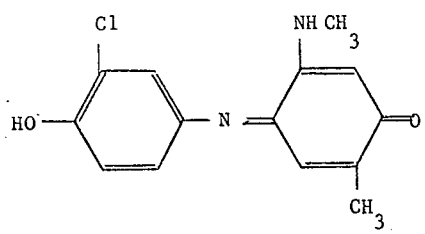

There is dissolved 0.01 mole (1.37 g) of 2-methyl-5-methylamino phenol in 15 cc of acetone to which is added 10 cc of ammonia (22°Be.). Finally there is dissolved 0.01 mole (1.80 g) of 2-chloro-4-amino phenol monohydrochloride in 25 cc of water. The two resulting solutions are mixed together and while maintaining the temperature of the resulting mixture at about 0°C, there is added thereto, little by little, 0.02 mole (4.6 g) of ammonium persulfate in solution in 15 cc of water. At the end of this addition step the reaction mixture is filtered to recover the above indophenol which is then washed with water, with agitation, the wash water containing sufficient acetic acid to impart to the same a pH of about 6. The indophenol is filtered from the wash medium, washed again with water and recrystallized in a mixture of water and acetone. After drying under a vacuum the resulting indophenol exhibits a melting point of about 226°C.

| Analysis | Calculated for $C_{14}H_{13}N_2ClO_2$ | Found | |
|---|---|---|---|
| C% | 60.76 | 59.98 | 60.20 |
| H% | 4.70 | 4.92 | 5.0 |
| N% | 10.12 | 10.05 | 10.00 |
| Cl% | 12.84 | 12.68 | 12.74 |

EXAMPLE 35

The N-[(4'-hydroxy-3'-chloro) phenyl]-2,6-dimethyl-3-ureido benzoquinone imine of example 18 is prepared in accordance with the following reaction scheme:

There is dissolved 0.2 mole (36 g) of 2,6-dimethyl-3-ureido phenol in one liter of isopropyl alcohol to which has been added one liter of ammonia (22°Be). There is then dissolved 0.22 mole (39.6 g) of 2-chloro-4-amino phenol monohydrochloride in 500 cc of water. The two solutions are then mixed and to the resulting mixture there are added, initially, 1.5 kg of crushed ice and then, little by little, with good agitation, 0.44 mole (101 g) of ammonium persulfate in solution in 300 cc of water. At the end of this addition step, the above indophenol is precipitated by neutralizing the reaction medium with acetic acid. The crude indophenol is recovered therefrom by filtering the reaction medium and is then washed with water, recrystallized from a mixture of pyridine and water and dried under a vacuum. It exhibits a melting point of 199°C.

| Analysis | Calculated for $C_{15}H_{14}O_3N_3Cl$ | Found | |
|---|---|---|---|
| C% | 56.34 | 56.15 | 55.92 |
| H% | 4.36 | 4.51 | 4.47 |
| N% | 13.16 | 13.21 | 13.06 |
| Cl% | 11.11 | 11.31 | |

EXAMPLE 36

The N-[(4'-hydroxy-3'-chloro) phenyl]-2-chloro-5-amino benzoquinone imine of example 19 is prepared in accordance with the following reaction scheme:

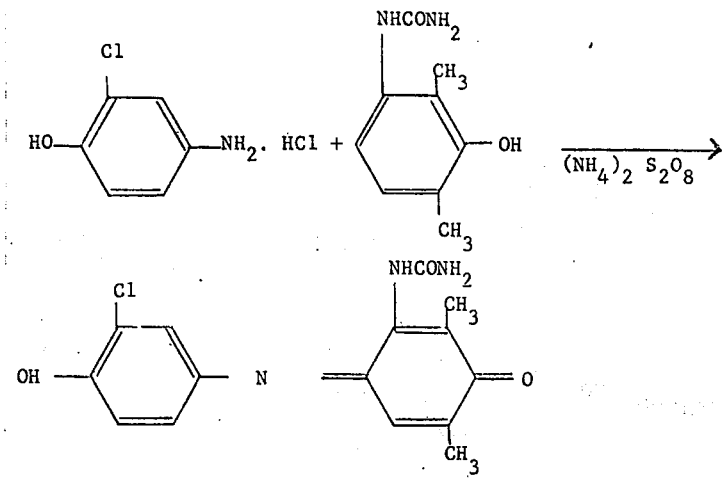

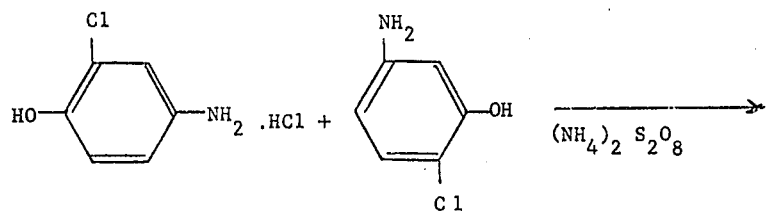

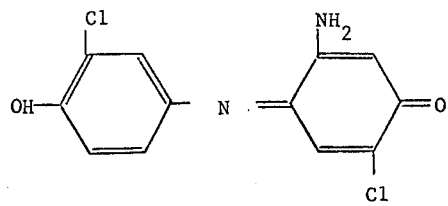

There is dissolved 0.01 mole (1.43 g) of 2-chloro-5-amino phenol in 15 cc of acetone to which is added 10 cc of ammonia (22°Be). There is then dissolved 0.01 mole (1.80 g) of 2-chloro-4-amino phenol monohydrochloride in 25 cc of water. The two solutions are then mixed together and while maintaining the temperature of the resulting mixture about 0°C. there is added, little by little, 0.02 mole (4.6 g) of ammonium persulfate on 25 cc of water. At the end of this addition step, the reaction mixture is filtered to recover the above indophenol which is washed first in a weakly acetic acid solution, then in a pure water medium and finally with a little acetone. After drying under a vacuum, the above indophenol exhibits a melting point of 252°C.

| Analysis | Calculated for $C_{12}H_8 N_2Cl_2O_2$ | Found | |
|---|---|---|---|
| C% | 50.89 | 50.55 | 50.64 |
| H% | 2.82 | 3.05 | 3.19 |
| N% | 9.88 | 10.04 | 10.15 |
| Cl% | 25.09 | 24.83 | 24.95 |

EXAMPLE 37

The N-[(4'-hydroxy) phenyl]-3-amino-2,6-dimethyl benzoquinone imine of example 20 is prepared in accordance with the following reaction scheme:

A first solution is prepared by dissolving 0.02 mole (2.18 g) of paraaminophenol in 200 cm³ of a 0.1 N NaOH solution. A second solution is prepared by dissolving 0.01 mole (1.37 g) of 2,6-dimethyl-3-amino phenol also in 100 cm³ of 0.1 N NaOH solution. The two solutions are mixed and air is bubbles for 2 hours in the resulting mixture at ambient temperature. The pH of the reaction mass in then brought to 5 by addition of an aqueous hydrochloric acid solution. The reaction mass is then filtered off to produce 2.12 g of said indophenol which, after recrystallization in a dimethylformamide-water mixture, melts at 248°C.

| Analysis | Calculated for $C_{14}H_{14} N_2O_2$ | Found | |
|---|---|---|---|
| C% | 69.42 | 69.38 | 68.78 |
| H% | 5.78 | 5.83 | 6.00 |
| N% | 11.57 | 11.70 | 11.67 |

EXAMPLE 38

The N-[(4'-hydroxy-2'-chloro) phenyl]-2-methyl-5-ureido benzoquinone imine of example 15 is prepared according the following reaction scheme:

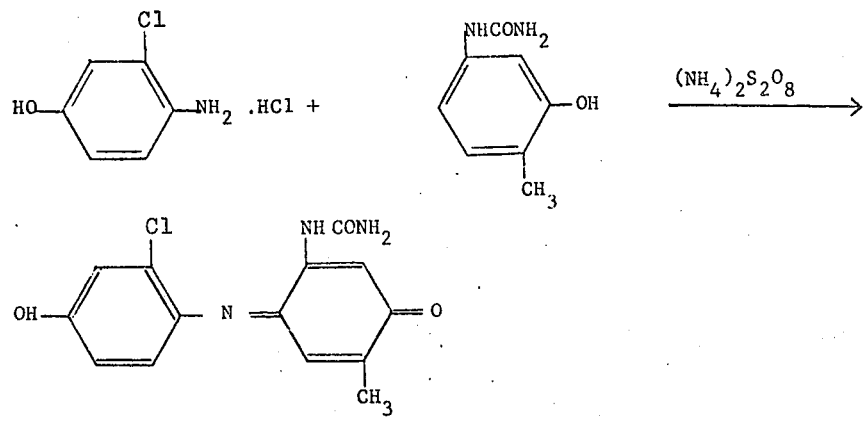

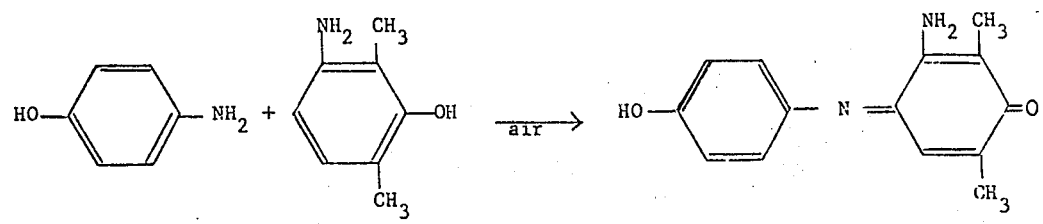

There is dissolved, on the one hand, 0.2 mole (33.2 g) of 2-methyl-5-ureido phenol in one liter of isopropyl alcohol to which has been added one liter of ammonia (22°Be), and on the other hand 0.22 mole (39.6 g) of 3-chloro-4-amino phenol monohydrochloride in 600 cc of water to which 30 cc of H Cl (d = 1.18) have been added. The resulting two solutions are mixed together and to the mixture there are added 1.6 kg of crushed ice and then, little by little, with agitation, 0.44 mole (101 g) of ammonium persulfate in 300 cc of water. At the end of this addition step the reaction mixture is filtered to recover the crude indophenol which is then washed in 1 liter of water, the pH of which has been adjusted to 6 with acetic acid. The wash medium is filtered to recover the indophenol which is then washed with water and recrystallized from a mixture of dimethylformamide and water. After drying under a vacuum the product melts with decomposition at 260°C.

| Analysis | Calculated for $C_{14}H_{12}O_3N_3Cl$ | Found | |
|---|---|---|---|
| C% | 55.00 | 55.06 | 54.97 |
| H% | 3.93 | 3.99 | 4.00 |
| N% | 13.74 | 13.93 | 13.90 |

EXAMPLE 39

The N-[(4'-amino-3'-methyl) phenyl]-3-carbamylmethylamino-6-methyl benzoquinone imine of example 16 is prepared in accordance with the following reaction scheme:

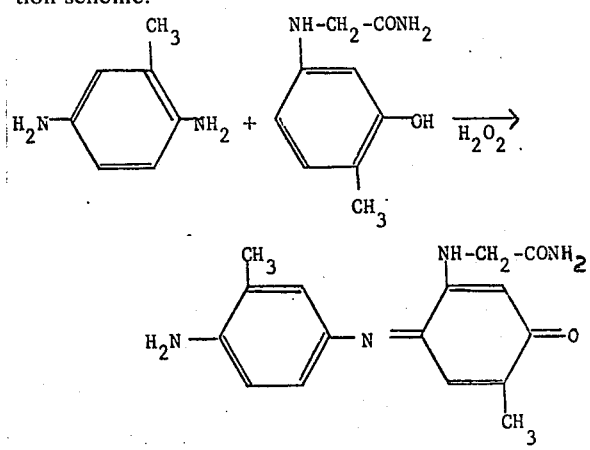

0.1 mole (19.5 g) paratoluylenediamine dichlorhydrate is dissolved in 400 cc water. The pH of this solution is adjusted to 8 by addition thereto of ammonia. This solution is immediately added to 0.04 mole (7.2 g) N-5-carbamylmethylamino-2-methyl phenol previously dissolved in 400 cc water. 100 cc ammonia 22°Be and 500 cc hydrogen peroxide to make 20 volumes are then added to this mixture which is allowed to stand for five hours at ambient temperature. 7.40 g of the above indoaniline in crystalline form are recovered by filtering the reaction mixture on a suction filter. After washing with water and recrystallization from a pyridine and water mixture, the resulting indoaniline exhibited a melting point of 199°C.

| Analysis | Calculated for $C_{16}H_{18}O_2N_4$ | Found |
|---|---|---|
| C% | 64.43 | 63.98 |
| H% | 6.04 | 6.08 |

EXAMPLE 40

A hair dye composition is prepared as follows:

| | |
|---|---|
| The diphenylamine leucoderivative of Example 3 | 0.15 g |
| Hydroxyethylcellulose | 2 g |
| Triethanolamine sufficient for | pH 10 |
| Water sufficient for | 100 g |

Gray hair is impregnated with this hair dye composition and after 20 minutes exposure to the air, the hair is rinsed, then shampooed. A gray coloring with lilac glints is imparted thereto.

EXAMPLE 41

A hair dye composition is prepared as follows:

| | |
|---|---|
| The diphenylamine leucoderivative of Example 2 | 0.05 g |
| Hydroxyethylcellulose | 2 g |
| Triethanolamine sufficient for | pH 10 |
| Water sufficient for | 100 g |

Beached hair is impregnated with this hair dye composition and after 20 minutes exposure to the air, followed by rinsing and shompooing, a periwinkle blue coloring is imparted thereto.

EXAMPLE 42

The following hair dye composition is prepared:

| | |
|---|---|
| The diphenylamine leucoderivative of Example 5 | 0.2 g |
| Ethylene diamine tetraacetic acid | 0.3 g |
| Ammonium thioglycolate | 0.5 g |
| Ammonia sufficient for | pH 8 |
| Water sufficient for | 100 g |

Gray hair is impregnated with this hair dye composition and after 20 minutes exposure to the air, the hair is rinsed and shampooed. A very clear chestnut coloring is imparted thereto.

EXAMPLE 43

A hair dye composition is prepared as follows:

| | |
|---|---|
| The diphenylamine leucoderivative of Example 1 | 0.03 g |
| Hydroxyethylcellulose | 2 g |
| Triethanolamine sufficient for | pH 10 |
| Water sufficient for | 100 g |

Bleached hair is impregnated with this hair dye composition and after 20 minutes exposure to the air, the hair is rinsed and then shampooed. A platinum coloring with blue glints is imparted thereto.

EXAMPLE 44

A hair dye composition is prepared as follows:

| | |
|---|---|
| The diphenylamine leucoderivative of Example 6 | 0.2 g |
| Hydroxyethylcellulose | 2 g |
| Triethanolamine sufficient for | pH 9 |
| Water sufficient for | 100 g |

Bleached hair is impregnated with this hair dye composition and after 20 minutes exposure to the air, the hair is rinsed and then shampooed. A clear golden copper coloring is imparted thereto.

EXAMPLE 45

A hair dye composition is prepared as follows:

| | |
|---|---|
| The diphenylamine leucoderivative of Example 5 | 0.4 g |
| N,N-4-dimethylamine-2'-4'-diamino-5'-methyl-diphenylamine trihydrochloride, monohydrate | 0.1 g |
| Ammonia sufficient for | pH 11 |
| Water sufficient for | 100 cm$^3$ |

Gray hair is impregnated with this hair dye composition and after 20 minutes exposure to the air, the hair is rinsed and then shampooed. A frosted chestnut coloring is imparted thereto.

EXAMPLE 46

A hair dye composition is prepared as follows:

| | |
|---|---|
| The diphenylamine leucoderivative of Example 4 | 0.04 g |
| 4-hydroxy-2',4'-diamino-5'-methoxy-diphenylamine dihydrochloride, monohydrate | 0.06 g |
| Ammonia sufficient for | pH 11 |
| Water sufficient for | 100 g |

Gray hair is impregnated with this hair dye composition and after 20 minutes exposure to the air, followed by rinsing and shampooing, a very clear plum coloring with iridescent glints is obtained.

EXAMPLE 47

A hair setting lotion is prepared as follows:

| | |
|---|---|
| The diphenylamine leucoderivative of Example 6 | 0.1 g |
| Crotonic acid-vinyl acetate copolymer 10%:90% | 2 g |
| Ethanol, 95° titer sufficient for | 50° |
| Triethanolamine sufficient for | pH 9 |
| Water sufficient for | 100 g |

This composition applied as a hair-setting solution to bleached hair gives it a tea rose shade.

EXAMPLE 48

A hair-setting solution is prepared as follows:

| | |
|---|---|
| The diphenylamine leucoderivative of Example 6 | 0.08 g |
| 4-hydroxy-N,N-4'-dimethylamino-diphenylamine | 0.02 g |
| Crotonic acid-vinyl acetate copolymer 10% : 90% | 2 g |
| Ethanol, 95° titer, sufficient for | 50° |
| Triethanolamine sufficient for | pH 9 |
| Water sufficient for | 100 |

This composition, applied as a hair-setting lotion to bleached hair, gives it a very clear copper shade.

EXAMPLE 49

A hair-setting lotion is prepared as follows:

| | |
|---|---|
| The diphenylamine leucoderivative of Example 3 | 0.1 g |
| Crotonic acid-vinyl acetate copolymer 10% : 90% | 2 g |
| Ethanol, 95° titer, sufficient for | 50° |
| Triethanolamine sufficient for | pH 9 |
| Water sufficient for | 100 g |

This composition, applied as a hair-setting lotion to bleached hair, gives it a clear violet shade.

EXAMPLE 50

A hait-setting lotion is prepared as follows:

| | |
|---|---|
| The diphenylamine leucoderivative of Eample 3 | 0.05 g |
| Crotonic acid-vinyl acetate copolymer 10% : 90% | 2 g |
| Ethanol, 95° titer sufficient for | 50° |
| Triethanolamine sufficient for | pH 9 |
| Water sufficient for | 100 g |

This composition, applied to gray hair as a hair-setting lotion, gives it a beige coloring with violet glints.

EXAMPLE 51

A hair-setting lotion is prepared as follows:

| | |
|---|---|
| The diphenylamine leucoderivative of Example 3 | 0.05 g |
| Crotonic acid-vinyl acetate copolymer 10% : 90% | 2 g |
| Ethanol, 95° titer sufficient for | 50° |
| Triethanolamine sufficient for | pH 7 |
| Water sufficient for | 100 |

This composition, applied as a hair-setting lotion to bleached hair, gives it a clear beige shade with salmon glints.

EXAMPLE 52

A hair-setting lotion is prepared as follows:

| | |
|---|---|
| The diphenylamine leucoderivative of Example 4 | 0.05 g |
| Crotonic acid-vinyl acetate copolymer 10% : 90% | 2 g |
| Ethanol, 95° titer sufficient for | 50° |
| Triethanolamine sufficient for | pH 7 |
| Water sufficient for | 100 g |

This composition, applied to bleached hair as a hair-setting lotion, gives it a clear silvered gray shade.

EXAMPLE 53

A hair-setting lotion is prepared as follows:

| | |
|---|---|
| The diphenylamine leucoderivative of Example 4 | 0.025 g |
| 4-hydroxy-2', 4'diamino-5'-methoxy-diphenylamine trihydrochloride monohydrate | 0.025 g |
| Crotonic acid-vinyl acetate copolymer 10% : 90% | 2 g |
| Ethanol, 95° titer, sufficient for | 50° |
| Triethanolamine sufficient for | pH 9 |
| Water sufficient for | 100 |

This composition, applied to bleached hair as a hair-setting lotion, gives it a clear beige shade with pearl glints.

EXAMPLE 54

A hair-setting lotion is prepared as follows:

| | |
|---|---|
| The diphenylamine leucoderivative of Example 4 | 0.025 g |
| 4,4'-dihydroxy-3,5-dimethyl-diphenylamine | 0.025 g |
| Crotonic acid-vinyl acetate copolymer | 2 g |
| Ethanol, 95° titer sufficient for | 50° |
| Triethanolamine sufficient for | pH 7 |
| Water sufficient for | 100 g |

This composition, applied to bleached hair as a hair-setting lotion, gives it a very clear blond shade with pearl glints.

EXAMPLE 55

A hair dye composition is prepared as follows:

| | |
|---|---|
| The diphenylamine leucoderivative of Example 3 | 0.1 g |
| Sodium laurylsulfate with 20% oxyethylenated lauryl alcohol | 20 g |
| Ethylene diamine tetraacetic acid | 2 g |
| Ammonia sufficient for | pH 10.5 |
| Water sufficient for | 100 g |

Bleached hair is impregnated with this hair dye solution. After 20 minutes of exposure to the air, the hair is rinsed, then shampooed. A cyclamen shade is obtained.

EXAMPLE 56

A hair-setting lotion is prepared as follows:

| | |
|---|---|
| The diphenylamine leucoderivative of Example 1 | 0.05 g |
| Crotonic acid-vinyl acetate copolymer | 2 g |
| Ethanol, 95° titer, sufficient for | 50° |
| Triethanolamine sufficient for | pH 9 |
| Water sufficient for | 100 g |

This composition, applied to bleached hair as a hair-setting lotion gives it a silver gray shade with lavender glints.

EXAMPLE 57

A hair-setting lotion is prepared as follows:

| | |
|---|---|
| The diphenylamine leucoderivative of Example 2 | 0.05 g |
| Crotonic acid-vinyl acetate copolymer | 2 g |
| Ethanol, 95° titer, sufficient for | 50° |
| Triethanolamine sufficient for | pH 9 |
| Water sufficient for | 100 g |

This composition, applied to bleached hair as a hair-setting lotion, gives it a gray tint with blue green glints.

EXAMPLE 58

A hair-setting lotion is prepared as follows:

| | |
|---|---|
| The diphenylamine leucoderivative of Example 6 | 0.02 g |
| Crotonic acid-vinyl acetate copolymer | 2 g |
| Ethanol, 95° titer sufficient for | 50° |
| Triethanolamine sufficient for | pH 9 |
| Water sufficient for | 100 g |

This composition, applied to bleached hair as a hair-setting lotion, gives it a golden apricot tint.

EXAMPLE 59

A hair dye composition is prepared as follows:

| | |
|---|---|
| The diphenylamine leucoderivative of Example 2 | 0.1 g |
| Hydroxyethylcellulose | 1 g |
| Triethanolamine sufficient for | pH 10 |
| 20 volume hydrogen peroxide | 50 cm³ |
| Water sufficient for | 100 g |

Gray hair is impregnated with this hair dye composition and after 20 minutes the hair is rinsed and then shampooed. A slate gray coloring is imparted thereto.

EXAMPLE 60

A hair dye composition is prepared as follows:

| | |
|---|---|
| The diphenylamine leucoderivative of Example 6 | 0.025 g |
| 4-hydroxy-N,N-4'-dimethylamino-diphenylamine | 0.1 g |
| Hydroxyethylcellulose | 1 g |
| Triethanolamine sufficient for | pH 10 |
| 20 volume hydrogen peroxide | 50 cm³ |
| Water sufficient for | 100 g |

Gray hair is impregnated with this hair dye composition and after 20 minutes the hair is rinsed and then shampooed. A verdigris shade is imparted thereto.

EXAMPLE 61

The following hair dye composition is prepared:

| | |
|---|---|
| The diphenylamine leucoderivative of Example 13 | 0.04 g |
| Isopropylic alcohol | 25 g |
| Polyvinylpyrrolidone-vinyl acetate copolymer 70/30 M.W. 40.000 | 1.5 g |
| Monoethanolamine sufficient for pH 7.5 | |
| Water sufficient for | 100 g |

This composition applied as a hair-setting lotion to gray hair gives it a silvered gray shade,

EXAMPLE 62

The following hair dye composition is prepared:

| | |
|---|---|
| The diphenylamine leucoderivative of Example 11 | 0.06 g |
| Ethanol 96° | 30 g |
| Polyvinylpyrrolidone-vinylacetate copolymer 60/40 | 2 g |
| Triethanolamine sufficient for pH 8 | |
| Water sufficient for | 100 g |

This composition applied as a hair-setting lotion to bleached hair gives it peach shade.

EXAMPLE 63

The following hair dye composition is prepared:

| | |
|---|---|
| 3.5-diemthyl-4-hydroxy-4'-amino diphenylamine | 0.08 g |
| Isopropanol | 35 g |
| Polyvinylpyrrolidone M.W. 40.000 | 2.5 g |
| 2-amino-2-methyl propanol sufficient for pH 8.5 | |
| Water sufficient for | 100 g |

This composition applied as a hair-setting lotion to gray hair gives it a violet shade.

EXAMPLE 64

The following hair dye composition is prepared:

| | |
|---|---|
| The diphenylamine leucoderivative of example 18 | 0.1 g |
| Isopropanol | 40 g |
| Vinylacetate-allyl stearate-allyl-oxyacetic acid terpolymer in the proportion 80%-15%-5% | 3 g |
| Ammonia sufficient for pH 9 | |
| Water sufficient for | 100 g |

The composition applied as a hair setting lotion to bleached hair gives it a pink sand shade.

EXAMPLE 65

The following hair dye composition is prepared:

| | |
|---|---|
| The diphenylamine leucoderivative of example 8 | 0.12 g |
| Ethanol 96° | 45 g |
| Methyl methacrylate-stearyl methacrylate - dimethyl methacrylate terpolymer in the proportions 20%-23%-57% | 1.25 g |
| Monoethanolamine sufficient for pH 9.5 | |
| Water sufficient for | 100 g |

This composition applied as a hair setting lotion to white hair gives it a cloud shade.

EXAMPLE 66

The following hair dye composition is prepared:

| | |
|---|---|
| 2',3,5,6'-tetramethyl-4,4'-dihydroxy diphenylamine | 0.14 g |
| Ethanol 96° | 50 g |
| Polyvinylpyrrolidone-vinylacetate copolymer 30%/70% M.W. 160,000 | 3 g |
| Triethanolamine sufficient for pH 10 | |
| Water sufficient for | 100 g |

This composition applied as a hair setting lotion to bleached hair gives it a pink beige shade subduing the yellow of the bleached hair.

EXAMPLE 67

The following hair dye composition is prepared:

| | |
|---|---|
| The diphenylamine leucoderivative of example 9 | 0.16 g |
| Isopropanol | 48 g |
| Polyvinylpyrrolidone-vinylacetate copolymer 70%–30% M.W. 40,000 | 2.8 g |
| 2-amino-2-methyl propanol sufficient for pH 9.8 | |
| Water sufficient for | 100 g |

The composition applied as a hair setting lotion to gray hair gives it a bluish gray shade.

EXAMPLE 68

The following hair dye composition is prepared:

| | |
|---|---|
| 3,3',5,5'-tetramethyl-4-hydroxy-4'-amino diphenylamine | 0.18 g |
| Ethanol 96° | 46 g |
| Polyvinylpyrrolidone-vinylacetate copolymer 60%–40% | 2.5 g |
| Ammonia sufficient for pH 9.6 | |
| Water sufficient for | 100 g |

The composition applied as a hair setting lotion to gray hair gives it a violet gray shade.

EXAMPLE 69

The following hair dye composition is prepared:

| | |
|---|---|
| The diphenylamine leucoderivative of example 19 | 0.2 g |
| Isopropanol | 45 g |
| Polyvinylpyrrolidone | 2 g |
| Triethanolamine sufficient for pH 9.2 | |
| Water sufficient for | 100 g |

The composition applied as a hair setting lotion to bleached hair gives it a pink sand shade.

EXAMPLE 70

The following hair dye composition is prepared:

| | |
|---|---|
| 2-acetylamino-4-hydroxy-2'-methoxy-4'-amino-5'-methyl diphenylamine | 0.19 g |
| Isopropanol | 43 g |
| vinyl acetate-allyl stearate - allyloxy acetic acid terpolymer in the proportions 80%–15%–5% | 2.2 g |
| Monoethanolamine sufficient for pH 9.5 | |
| Water sufficient for | 100 g |

The composition applied as a hair setting lotion to gray hair gives it a light grayish green shade.

EXAMPLE 71

The following hair dye composition is prepared:

| | |
|---|---|
| The diphenylamine leucoderivative of example 20 | 0.14 g |
| Isopropanol | 37 g |
| Polyvinylpyrrolidone-vinylacetate copolymer 70%–30% M.W. 40.000 | 1.7 g |
| Monoethanolamine sufficient for pH 8.4 | |
| Water sufficient for | 100 g |

This composition applied as a hair setting lotion to white hair gives it an apricot shade.

EXAMPLE 72

The following hair dye composition is prepared:

| | |
|---|---|
| The diphenylamine leucoderivative of example 16 | 0.13 g |
| Ethanol 96° | 36 g |
| Polyvinylpyrrolidone-vinylacetate copolymer 60%–40% | 1.6 g |
| Triethanolamine sufficient for pH 8.6 | |
| Water sufficient for | 100 g |

This composition applied as a hair setting lotion to white hair gives it an old rose shade.

EXAMPLE 73

The following hair dye composition is prepared:

| | |
|---|---|
| The diphenylamine leucoderivative of example 17 | 0.12 g |
| Isopropanol | 34 g |
| Polyvinylpyrrolidone M.W. 40,000 | 1.4 g |
| 2-amino-2-methylpropanol sufficient for pH 8.3 | |
| Water sufficient for | 100 g |

The composition applied as a hair setting lotion to gray hair gives it a bright grayish orange shade.

EXAMPLE 74

The following hair dye composition is prepared:

| | |
|---|---|
| 3,5,2'-trimethyl-4-hydroxy-4'-amino diphenylamine | 0.11 g |
| Ethanol 96° | 50 g |
| Vinyl acetate-allyl stearate-allyloxy acetic acid terpolymer in the proportions 80%–15%–5% | 1.3 g |
| Ammonia sufficient for pH 8.2 | |
| Water sufficient for | 100 g |

The composition applied as a hair setting lotion to white hair gives it a grayish mauve shade.

EXAMPLE 75

The following hair dye composition is prepared:

| | |
|---|---|
| The diphenylamine leucoderivative of example 15 | 0.09 g |
| Isopropanol | 29 g |
| Polyvinylpyrrolidone-vinylacetate copolymer 30%–70% M.W. 160,000 | 1.2 g |
| Monoethanolamine sufficient for pH 10 | |
| Water sufficient for | 100 g |

The composition applied as a hair setting lotion to bleached hair gives it a golden beige shade.

EXAMPLE 76

The following hair dye composition is prepared:

| | |
|---|---|
| The diphenylamine leucoderivative of example 14 | 0.03 g |
| Polyvinylpyrrolidone M.W.40,000 | 1.9 g |
| Ethanol 96° | 22 g |
| Ammonia sufficient for pH 7.2 | |
| Water sufficient for | 100 g |

The composition is applied as a hair setting lotion to white hair gives it a rosetree shade.

EXAMPLE 77

The following hair dye composition is prepared:

| | |
|---|---|
| 2,3'-dichloro-5-acetylamino-4,4'-dihydroxy diphenylamine | 0.1 g |
| Polyvinylpyrrolidone M.W. 40,000 | 2 g |
| Ethanol 96° | 30 g |
| Ammonia sufficient for pH 7.1 | |
| Water sufficient for | 100 g |

The composition applied as a hair setting lotion to white hair gives it a pink blond shade.

EXAMPLE 78

The following hair dye composition is prepared:

| | |
|---|---|
| The diphenylamine leucoderivative of example 7 | 0.08 g |
| Polyvinylpyrrolidone-vinylacetate copolymer 60%–40% | 1 g |
| Isopropanol | 40 g |
| 2-amino-2-methylpropanol sufficient for pH 9.8 | |
| Water sufficient for | 100 g |

This composition applied as a hair setting lotion to white hair gives it a pistachio shade.

EXAMPLE 79

The following hair dye composition is prepared:

| | |
|---|---|
| The diphenylamine leucoderivative of example 17 | 0.2 g |
| Lauryl ammonium sulfate | 20 g |
| 2-amino-2-methyl propanol sufficient for pH 9 | |
| Water sufficient for | 100 g |

Bleached hair is impregnated with this hair dye solution and after 25 minutes exposure to the air, followed by rinsing, shampooing and rinsing, a light golden apricot shade is obtained.

EXAMPLE 80

The following hair dye composition is prepared:

| | |
|---|---|
| 3,5-dimethyl-4-hydroxy-4'-amino diphenylamine | 0.08 g |
| Hydroxyethylcellulose | 2 g |
| Ammonia sufficient for pH 8.5 | |
| Water sufficient for | 100 g |

This composition mixed with an equal weight of 6% hydrogen peroxide and applied for 30 minutes to white hair produces mauve shade with silvery glints.

EXAMPLE 81

The following hair dye composition is prepared:

| | |
|---|---|
| The diphenylamine leucoderivative of example 16 | 0.5 g |
| Ethylene diamine tetraacetic acid | 0.3 g |
| Monoethanolamine sufficient for pH 10.2 | |
| Water sufficient for | 100 g |

This composition mixed with an equal weight of 6% hydrogen peroxide and applied for 5 minutes to gray hair produces a grayish rose ashy shade.

EXAMPLE 82

The following hair dye composition is prepared:

| | |
|---|---|
| The diphenylamine leucoderivative of example 9 | 0.3 g |
| Ammonium thioglycolate | 0.5 g |
| Ethylene diamine tetraacetic acid | 0.3 g |
| Ammonia sufficient for pH 9.8 | |
| Water sufficient for | 100 g |

Bleached hair is impregnated with this hair dye solution and after 10 minutes exposure to the air, followed by rinsing, shampooing and rinsing, a glacier blue shade is obtained.

EXAMPLE 83

The following hair dye composition is prepared:

| | |
|---|---|
| The diphenylamine leucoderivative of example 14 | 0.05 g |
| Ammonium thioglycolate | 0.5 g |
| Ethylene diamine tetraacetic acid | 0.3 g |
| Triethanolamine sufficient for pH 7.5 | |
| Water sufficient for | 100 g |

Gray hair is impregnated with this hair dye solution and after 15 minutes exposure to the air, followed by rinsing, shampooing and rinsing, a light pink ashy shade is obtained.

EXAMPLE 84

The following hair dye composition is prepared:

| | |
|---|---|
| The diphenylamine leucoderivative of example 7 | 0.1 g |
| Hydroxyethylcellulose | 2 g |
| Monoethanolamine sufficient for pH 11 | |
| Water sufficient for | 100 g |

Gray hair is impregnated with this hair dye solution and after 20 minutes exposure to the air, followed by rinsing, shampooing and rinsing, a pearly medium green shade is obtained.

EXAMPLE 85

The following hair dye composition is prepared:

| | |
|---|---|
| The diphenylamine leucoderivative of example 12 | 0.1 g |
| The diphenylamine leucoderivative of example 10 | 0.1 g |
| The diphenylamine leucoderivative of example 13 | 0.1 g |
| Butylglycol | 5 g |
| Ammonia sufficient for pH 11 | |
| Water sufficient for | 100 g |

Gray hair is impregnated with this hair dye solution and after 25 minutes exposure to the air, followed by rinsing, shampooing and rinsing a silvery wistaria shade is obtained.

EXAMPLE 86

The following hair dye composition is prepared:

| | |
|---|---|
| 3,5-diphenyl-4-4'-dihydroxy diphenylamine hydrochloride | 0.2 g |
| 2,3'-dichloro-5-acetylamino-4,4'-dihydroxy diphenylamine | 0.2 g |
| Butylglycol | 5 g |
| Triethanolamine sufficient for pH 9 | |
| Water sufficient for | 100 g |

White hair is impregnated with this hair dye solution and after 15 minutes exposure to the air, followed by rinsing, shampooing and rinsing a geranium shade is obtained.

EXAMPLE 87

The following hair dye composition is prepared:

| | |
|---|---|
| The diphenylamine leucoderivative of example 8 | 0.05 g |
| 3,5-dimethyl-4-hydroxy-4'-amino diphenylamine | 0.1 g |
| 3,5-dimethyl-4,4'-dihydroxy-2'-chloro diphenylamine | 0.3 g |
| Butylglycol | 5 g |
| Sodium carbonate sufficient for pH 8 | |
| Water sufficient for | 100 g |

Gray hair is impregnated with this hair dye solution and after 30 minutes exposure to the air, followed by rinsing, shampooing and rinsing, an ashy wistaria shade is obtained.

What is claimed is:

1. Diphenylamine having the formula:

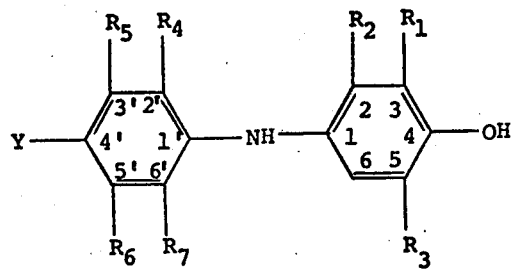

wherein
Y represents a member selected from the group consisting of hydroxy and amino;
$R_1$ and $R_3$, each independently, represent a member selected from the group consisting of hydrogen, halogen, lower alkyl, and —NHCOR wherein R is lower alkyl;
$R_2$ represents a member selected from the group consisting of hydrogen, halogen, lower alkyl, —NHCOR wherein R is lower alkyl and —NHR$_8$ wherein R$_8$ represents a member selected from the group consisting of hydrogen, lower alkyl and carbamyl lower alkyl, with the proviso that when $R_2$ is —$NHR_8$, $R_3$ is not hydrogen;

$R_4$, $R_5$, $R_6$ and $R_7$ each independently represent a member selected from the group consisting of hydrogen, halogen, lower alkyl and lower alkoxy, with the proviso (1) that when Y is hydroxy, $R_2$ is not hydrogen, lower alkyl or alkoxy, (2) that when Y is amino at least two of $R_1$, $R_2$ and $R_3$ are other than hydrogen and $R_2$ is not hydrogen when $R_4$, $R_5$, $R_6$ and $R_7$ are all hydrogen and (3) that $R_1$ or $R_3$ is NHCOR wherein R has the meaning given above or $R_8$ is carbamyl lower alkyl.

2. The diphenylamines of claim 1 wherein $R_2$ is —NHCOR wherein R is lower alkyl.

3. The diphenylamines of claim 2 selected from the group consisting of
2-acetylamino-4-hydroxy-5-methyl-4'-amino-2'-methoxy-5'-methyl diphenylamine,
5,3',5'-trimethyl-4-hydroxy-2-acetylamino-4'-amino diphenylamine,
5-methyl-2-acetylamino-4-hydroxy-2'-methoxy-4'-amino diphenylamine,
2,5-diacetylamino-4,4'-hydroxy-2'-chloro diphenylamine,
3,5-dimethyl-4,4'-dihydroxy-2-acetylamino diphenylamine,
5-methyl-4-hydroxy-2-acetylamino-4'-hydroxy diphenylamine and
5-methyl-4-hydroxy-2-acetylamino-4'-amino diphenylamine.

4. The diphenylamine of claim 3 which is 2-acetylamino-4-hydroxy-5-methyl-4'-amino-2'-methoxy-5'-methyl diphenylamine.

5. Diphenylamine having the formula

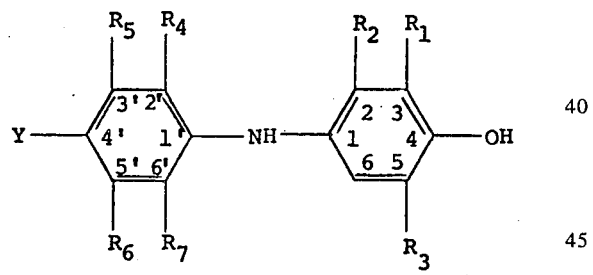

wherein
Y represents a member selected from the group consisting of hydroxy and amino;
$R_1$ and $R_3$, each independently, represent a member selected from the group consisting of hydrogen, halogen, lower alkyl and —NHCOR wherein R is lower alkyl;

$R_2$ is selected from the group consisting of halogen, —NHCOR wherein R is lower alkyl and —$NHR_8$ wherein $R_8$ is selected from the group consisting of hydrogen, lower alkyl and carbamyl lower alkyl with the proviso that (1) when $R_8$ is hydrogen one of $R_1$, $R_3$ and $R_4$–$R_7$ is halogen and (2) when $R_2$ is —$NHR_8$, $R_3$ is not hydrogen;

$R_4$, $R_5$, $R_6$ and $R_7$ each independently represent a member selected from the group consisting of hydrogen, halogen, lower alkyl and lower alkoxy, with the proviso that (1) when Y is hydroxy, $R_2$ is not halogen, and (2) when Y is amino, at least one of $R_1$ and $R_3$ is other than hydrogen; and the acid addition salt of said diphenylamine.

6. Diphenylamine having the formula

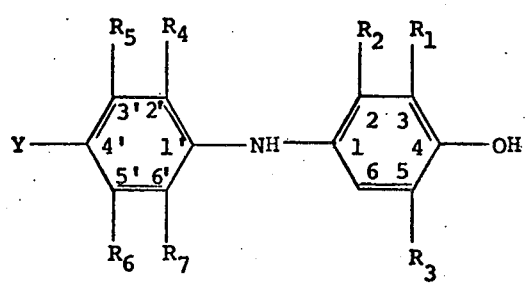

wherein
Y represents a member selected from the group consisting of hydroxy and amino;
$R_1$ and $R_3$, each independently, represent a member selected from the group consisting of hydrogen, halogen, lower alkyl and —NHCOR wherein R is lower alkyl;

$R_2$ is selected from the group consisting of halogen, —NHCOR wherein R is lower alkyl and —$NHR_8$ wherein $R_8$ is selected from the group consisting of lower alkyl and carbamyl lower alkyl, with the proviso that when $R_2$ is —$NHR_8$, $R_3$ is not hydrogen;

$R_4$, $R_5$, $R_6$ and $R_7$, each independently, represent a member selected from the group consisting of hydrogen, halogen, lower alkyl and lower alkoxy, with the proviso that (1) when Y is hydroxy, $R_2$ is not halogen, and (2) when Y is amino, at least one of $R_1$ and $R_3$ is other than hydrogen; and the acid addition salt of said diphenylamine.

* * * * *